United States Patent
Andersen

(10) Patent No.: US 12,215,135 B2
(45) Date of Patent: Feb. 4, 2025

(54) PDL2 COMPOUNDS

(71) Applicant: IO BIOTECH APS, Copenhagen (DK)

(72) Inventor: Mads Hald Andersen, Naerum (DK)

(73) Assignee: IO Biotech ApS, Copenhagen (DK)

( * ) Notice: Subject to any disclaimer, the term of this patent is extended or adjusted under 35 U.S.C. 154(b) by 0 days.

(21) Appl. No.: 17/819,280

(22) Filed: Aug. 11, 2022

(65) Prior Publication Data

US 2023/0227529 A1   Jul. 20, 2023

Related U.S. Application Data

(62) Division of application No. 16/911,996, filed on Jun. 25, 2020, now Pat. No. 11,447,537, which is a division of application No. 16/344,445, filed as application No. PCT/EP2017/076179 on Oct. 13, 2017, now abandoned.

(30) Foreign Application Priority Data

Oct. 27, 2016 (EP) .................... 16195949

(51) Int. Cl.
| | |
|---|---|
| C07K 14/705 | (2006.01) |
| A61K 39/00 | (2006.01) |
| A61K 39/39 | (2006.01) |
| A61P 35/00 | (2006.01) |
| A61K 38/00 | (2006.01) |
| A61K 45/06 | (2006.01) |

(52) U.S. Cl.
CPC ........ *C07K 14/70532* (2013.01); *A61K 39/39* (2013.01); *A61K 39/4611* (2023.05); *A61K 39/464411* (2023.05); *A61P 35/00* (2018.01); *A61K 38/00* (2013.01); *A61K 45/06* (2013.01)

(58) Field of Classification Search
CPC .......... C07K 14/70532; A61K 39/0011; A61K 39/39; A61K 38/00; A61K 45/06; A61P 35/00
See application file for complete search history.

(56) References Cited

U.S. PATENT DOCUMENTS

| | | | |
|---|---|---|---|
| 5,554,372 | A | 9/1996 | Hunter |
| 8,445,447 | B2 | 5/2013 | Chen |
| 11,447,537 | B2 | 9/2022 | Andersen |
| 2009/0042292 | A1 | 2/2009 | Chen |
| 2010/0055102 | A1 | 3/2010 | Langermann |

FOREIGN PATENT DOCUMENTS

| | | | |
|---|---|---|---|
| JP | 2012500847 A | | 1/2012 |
| JP | 2013512251 A | | 4/2013 |
| WO | WO-0202587 A1 | | 1/2002 |
| WO | WO-2009024531 A1 | | 2/2009 |
| WO | WO-2010027423 A2 | | 3/2010 |
| WO | WO-2010027827 A2 | | 3/2010 |
| WO | WO-2011066342 A2 | | 6/2011 |
| WO | WO-2015100219 A1 | | 7/2015 |
| WO | WO-2016168771 A2 | | 10/2016 |

OTHER PUBLICATIONS

Ahmad SM, et al., "Harnessing PD-L1-specific cytotoxic T cells for anti-leukemia immunotherapy to defeat mechanisms of immune escape mediated by the PD-1 pathway," Leukemia, vol. 28:236-238 (2014).
Andersen MH., "Immune Regulation by Self-Recognition: Novel Possibilities for Anticancer Immunotherapy," J Natl Cancer Inst., vol. 107:154: 8 pages. (2015).
Cancer immunotherapy immunoguiding program (CIP) assay guidelines (http://cimt.eu/ciml/files/dl/cip_guidelines.pdf), 4 pages.
Keilholz, U. et al., "Immunologic monitoring of cancer vaccine therapy: results of a workshop sponsored by the Society for Biological Therapy," J Immunolher., vol. 25: 97-138 (2002).
Larsen, SK, et al., "Functional characterization of Foxp3-specific spontaneous immune responses," Leukemia, vol. 27: 2332-2340 (2013).
Martinenaite E, et al., "CCL22-specific T cells: Modulating the Immunosuppressive Tumor Microenvironment," Oncoimmunology, vol. 5: e1238541, 10 pages (2016).
Mechanism of Carcinogenesis, Section 3, 2008, International agency for research on cancer, pp. 1-37.
Moodie Z, et al., "Response determination criteria for ELISPOT: toward a standard that can be applied across laboratories," Methods Mol Biol., vol. 792: 185-196 (2012).
Munir, S, et al., "Cutaneous T cell lymphoma cells are targets for immune checkpoint ligand PD-L1-specific, cytotoxic T cells," Leukemia, vol. 27:2251-2253 (2013).
Munir, S, et al., "HLA-restricted cytotoxic T cells that are specific for the immune checkpoint ligand PD-L1 occur with high frequency in cancer patients," Cancer Research, vol. 73:1674-1776 (2013).
Nazareth, M. et al., "Characterization of Human Lung Tumor-Associated Fibroblasts and Their Ability to Modulate the Activation of Tumor-Associated T Cells," J Immunol., vol. 178:5552-5562 (2007).
Ohigashi Y., et al., "Clinical Significance of Programmed Death-1 Ligand-1 and Programmed Death-1 Ligand-2 Expression in Human Esophageal Cancer," Clinical Cancer Research, Apr. 15, 2005, vol. 11, No. 8, pp. 2947-2953.
Rhee F "Idiotype vaccination strategies in myeloma: how to overcome a dysfunctional immune system," Clin Cancer Res, vol. 13: 1353-1355 (2007).
Solinas et al., Programmed cell death-ligand 2: A neglected but important target in the immune response to cancer?, Translational Oncology (2020) 13: 100811, 12 pages.

(Continued)

*Primary Examiner* — James H Alstrum-Acevedo
*Assistant Examiner* — Erinne R Dabkowski
(74) *Attorney, Agent, or Firm* — COOLEY LLP

(57) ABSTRACT

The present invention relates to a peptide compound of PDL2 selected from a peptide fragment, a functional homologue, and a functional analogue, as well as to a nucleic acid, such as DNA or RNA, encoding the peptide compound, a vector, such as a virus vector, and a host cell, such as mammalian cell, comprising the vector. The peptide compound, nucleic acid, vector and host cell of the present invention are in particular, useful for the treatment or prevention of a cancer characterized by expression of PDL2.

18 Claims, 6 Drawing Sheets

Specification includes a Sequence Listing.

(56) References Cited

OTHER PUBLICATIONS

Tokiyoshi Tanegashima, "Immune Suppression by PD-L2 against Spontaneous and Treatment-Related Antitumor Immunity," Clin Cancer Res 2019; vol. 25, pp. 4808-4819.

Wieczorek M. et al., "Major Histocompatibility Complex (MHC) Class I and MHC Class II Proteins: Conformational Plasticity in Antigen Presentation," Front. Immunol. (2017) 8:292, 16 pages.

Yearley et al., "PD-L2 Expression in Human Tumors: Relevance to Anti-PD-1 Therapy in Cancer," Clin Cancer Res. Jun. 2017, 23(12); 3158-3167.

Yearly, J et al, Proffered Paper Session on Immunotherapy in Cancer, EMSO European Cancer Congress 2015 "PD-L2 is expressed in various human tumour types and may explain the response seen to anti-PD-1 therapy in patients with tumours lacking PD-L1 expression," Sep. 27, 2015, http://www.esmo_org/Conferences/Past-Conferences/ European-Cancer-Congress-2015/News/Novel-Assay-Developed-to-Determine-PD-L2-Expression-in-Tumour-Samples), 10 pages.

Van Doorn et al., "Safety and tolerability evaluation of the use of Montanide ISATM51 as vaccine adjuvant: A systematic review," Human Vaccines & Immunotherapeutics, Jan. 2016, 12:1, 159-169.

PDL2 COMPOUNDS

RELATED APPLICATIONS

This application is a divisional of U.S. patent application Ser. No. 16/911,996, filed Jun. 25, 2020, which is a divisional of U.S. patent application Ser. No. 16/344,445, filed Apr. 24, 2019, which is a 35 U.S.C. 371 national stage filing of International Application No. PCT/EP2017/076179, filed Oct. 13, 2017, which claims priority to European Patent Application No. 16195949.9, filed Oct. 27, 2016, each of which is incorporated herein by reference in its entirety.

SEQUENCE LISTING

The Sequence Listing XML associated with this application is provided electronically in XML file format and is hereby incorporated by reference into the specification. The name of the XML file containing the Sequence Listing XML is IOBT_012_03US_SeqList_ST26. The XML file is 43,619 bytes, created on Jul. 28, 2022, and is being submitted electronically via USPTO Patent Center.

TECHNICAL FIELD

The present invention relates to novel peptide compounds, such as fragments of PDL2, as well as compositions, uses, and kit-of-parts comprising these peptide compounds. Furthermore, the invention concerns nucleic acids, vectors, and host cells expressing said peptide compounds, for use in a method for treatment or prevention of a cancer, either alone or when administered simultaneously or sequentially with an additional cancer therapy.

BACKGROUND ART

Molecules of the B7-CD28 family play an important role in T-cell activation and tolerance. These pathways are not only responsible for providing positive costimulatory signals to sustain T-cell activity, but also contribute inhibitory signals that modulate the magnitude of T-cell responses. Inhibitory molecules of the B7/CD28 family play a key role in the induction of immune tolerance in the tumor microenvironment. The programmed death-1 receptor (PD-1, CD279) with its ligands PD-L1 (CD274, B7-H1) and PD-L2 (CD273, B7-DC) constitutes one such inhibitory pathway. The relevance of the PD-1/PD-L1 pathway in cancer has been extensively studied and therapeutic approaches targeting PD-1 (e.g. nivolumab or pembrolizumab) and PD-L1 (e.g. avelumab or atezolizumab) have been developed and are already approved in several different indications of cancer. However, PD-L2 has not received as much attention and its role in modulating tumor immunity is less clear. It is known that PD-L2 is an inhibitory molecule, expressed not only by antigen-presenting cells, but also by other immune cells and nonimmune cells in an inducible manner, mainly through Th2-associated cytokines. Hence, the patterns of expression of PD-L1 and PD-L2 are quite distinct. PD-L1 is constitutively expressed by a wide variety of immune cells and nonimmune cells and most normal tissue cells seem to be able to upregulate PD-L1. PD-L2 expression was initially thought to be restricted to antigen-presenting cells such as macrophages and dendritic cells (DCs). In recent years however, several groups have shown that PD-L2 expression can be induced on a wide variety of other immune cells and nonimmune cells depending on microenvironmental stimuli. Importantly, PD-L2 expression has been reported in patients with cancer. Moreover, PD-L2 may be expressed within human tumours in the absence of PD-L1. This could impact the understanding of the effectiveness of different targeted therapies to anti-PD-1 therapy even in the absence of PD-L1 expression. Hence, PD-L2 expression has been described in several tumor types, including renal cell carcinoma, bladder carcinoma, melanoma, non-small-cell lung cancer (NSCLC), head and neck squamous carcinoma (HNSC), triple-negative breast cancer (TNBC), and gastric carcinoma. PD-L2 may be expressed in individual tumor samples even in the absence of PD-L1 (esmo.org/Conferences/Past-Conferences/European-Cancer-Congress-2015/News/Novel-Assay-Developed-to-Determine-PD-L2-Expression-in-Tumour-Samples).

Ohigashi et al. investigated the expression of PD-L1 and PD-L2 in human esophageal cancer to determine their clinical significance in patients' prognosis after surgery. Using RT-qPCR and immunohistochemistry, the authors showed that both PD-L1 and PD-L2 are expressed in frozen tissue samples of esophageal cancer patients and PD-L2-positive patients had a poorer prognosis than the negative patients, as was the case for PD-L1.

Interestingly, there was a significant inverse correlation between PD-L2 expression and CD8 TILs but not CD4 TILs. In a retrospective study involving 51 patients with pancreatic cancer, 27% of the analyzed tumors expressed PD-L2 versus 39% expressing PD-L1.

It is also important to note here that perhaps not only PD-L2 expression by the tumor cells themselves, but rather by stromal cells is of importance. Nazareth and colleagues found constitutively high PD-L1 and 2 expressions in fibroblasts that were cultured from human nonsmall-cell lung cancers. This expression appeared to be functional, since in vitro blocking studies demonstrated that the fibroblasts inhibited IFNγ-production by autologous T cells in a PD-L1- and 2-dependent manner. For this reason, future studies should not only focus on PD-L expression by tumor cells only, but also by the tumor stroma.

SUMMARY OF THE INVENTION

The present inventor has identified new immunogenic epitopes from extended PDL2 (human PDL2 including a signal sequence identified by SEQ ID NO 1 herein, reference NCBI accession Q9BQ51, version Q9BQ51.2). Several PD-L2 derived peptides were selected based on binding affinity to the tissue type HLA-A2, of these a smaller selection was further analyzed by ELISPOT, since at least part of the sequences of these peptides are either in the signal peptide part of the PD-L2 sequence or in the transmembrane domain of the PD-L2 protein sequence. The present inventor scrutinized peripheral blood mononuclear cells (PBMC) from nine cancer patients for the presence of specific T-cell responses against PD-L2-derived peptide using the IFN ELISPOT secretion assay. Strong responses were detected against some peptides and in particular, the response against one peptide was in addition readily detectable in healthy individuals (HD).

In one aspect, the present invention concerns a peptide fragment of a human PDL2 protein of SEQ ID NO: 1, which fragment is up to 100 amino acids in length and wherein the peptide fragment comprises or consists of a consecutive sequence in a range from 8 to 100 amino acids of SEQ ID NO: 1; or a pharmaceutically acceptable salt thereof.

The present invention also concerns a peptide fragment of a human PDL2 protein of SEQ ID NO: 1, which fragment is up to 100 amino acids in length and wherein the peptide fragment consists of a consecutive sequence in a range from 8 to 100 amino acids of SEQ ID NO: 1; or a pharmaceutically acceptable salt thereof.

In an embodiment the peptide fragment is up to 60 amino acids in length, such as up to 50 amino acids, up to 40 amino acids, or up to 30 amino acids in length. The corresponding upper range in the consecutive sequence is accordingly, 60, 50, 40 or 30 amino acids of SEQ ID NO: 1.

In a further embodiment the peptide is up to 21, 22, 23, 24, 25, 26, 27, 28, 29, or 30 amino acids in length.

In another embodiment the peptide fragment comprises or consists of a consecutive sequence in the range from 10 to 100 amino acids, such as from 10-17 amino acids, 20 to 30 amino acids, 30 to 40 amino acids, or from 40 to 50 amino acids.

In a further embodiment the peptide fragment consists of a consecutive sequence in the range from 10 to 100 amino acids, such as from 10-17 amino acids, 20 to 30 amino acids, 30 to 40 amino acids, or from 40 to 50 amino acids. Typically from 10-17 amino acids or from 20 to 100 amino acids.

In another embodiment the peptide fragment does not comprise amino acid 1-3 of SEQ ID NO 1, that is MIF. Studies of PDL2 did not reveal any significant effect of these 3 amino acids, and they do not contribute to activation of T-cells.

In a further embodiment the consecutive sequence comprises one or more sequences selected from any one of SEQ ID NO 2-12, such as any one of SEQ ID NO 2, 4, 11 and 12.

In one embodiment the consecutive sequence comprises both SEQ ID NO 2 and SEQ ID NO 4. For instance, the peptide fragment SEQ ID NO: 12 comprises both SEQ ID NO 2 and SEQ ID NO 4.

In a further embodiment the consecutive sequence comprises a sequence selected from SEQ ID NO 11, wherein the peptide fragment is up to 21, 22, 23, 24, 25, 26, 27, 28, 29, or 30 amino acids in length. Preferably, the consecutive sequence consist of SEQ ID NO 11.

In a still further embodiment the consecutive sequence comprises a sequence selected from SEQ ID NO 12, wherein the peptide fragment is up to 25, 26, 27, 28, 29, or 30 amino acids in length.

In a further embodiment the consecutive sequence comprises a sequence selected from SEQ ID NO 4, wherein the peptide fragment is up to 10, 11, 12, 13, 14, 15, 16, 17, 18, 19, 20, 21, 22, 23, 24, 25, 26, 27, 28, 29, or 30 amino acids in length.

In a still further embodiment the consecutive sequence comprises a sequence selected from SEQ ID NO 2, wherein the peptide fragment is up to 9, 10, 11, 12, 13, 14, 15, 16, 17, 18, 19, 20, 21, 22, 23, 24, 25, 26, 27, 28, 29, or 30 amino acids in length.

In a further embodiment the peptide fragment is capable of activating T-cells, such as CD4 and CD8 T-cells. Typically, the activation is determined by an ELISPOT assay, such as the ELISPOT assay described herein.

The C terminal amino acid may be in the form of the acid or the amide, both are contemplated as individual embodiments of the peptide fragment of the present invention.

Typically, the peptide fragment is an isolated, immunogenic peptide fragment.

In a further aspect the present invention relates to a composition comprising the peptide fragment of the present invention, optionally together with a pharmaceutically acceptable additive, such as carrier or adjuvant.

When the adjuvant is present, such adjuvant is preferably selected from the group consisting of bacterial DNA based adjuvants, oil/surfactant based adjuvants, viral dsRNA based adjuvants, imidazoquinolines, a Montanide ISA adjuvant.

In a further aspect the present invention relates to a peptide fragment of the present invention for use in the treatment of cancer, such as cancer characterized by expression of PDL2.

In a still further aspect the present invention relates to a method of treating or preventing cancer in a patient, the method comprising administering to the cancer patient an effective amount of the peptide fragment of the present invention. In an embodiment the method further comprises the simultaneous or sequential administration of an additional cancer therapy, such as a cytokine therapy, a T-cell therapy, an NK therapy, an immune system checkpoint inhibitor, chemotherapy, radiotherapy, immunostimulating substances, gene therapy, antibodies and dendritic cells. In a further embodiment the additional cancer therapy is selected from one or more of Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Nivolumab, Oxaliplatin, Paclitaxel, Pembrolizumab, Pemetrexed, Revlimid, Temozolomide, Teniposide, Thioguanine, Valrubicin, Vinblastine, Vincristine, Vindesine and Vinorelbine.

In a further aspect, the present invention concerns a nucleic acid, such as DNA or RNA, encoding the peptide fragment of the present invention.

In a still further aspect, the present invention concerns a vector, such virus vector, comprising the nucleic acid of the present invention.

In a further aspect, the present invention concerns a host cell, such as mammalian cell, comprising the vector of the present invention.

In a further aspect, the present invention relates to a kit-of-parts comprising:
  a) the composition of the present invention, and
  b) a composition comprising at least one second active ingredient, selected from an immunostimulating compound, such as an interleukin, e.g. IL-2 and or IL-21, an anti-cancer agent, such as a chemotherapeutic agent, e.g. Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, nivolumab, Oxaliplatin, Paclitaxel, pembrolizumab, Pemetrexed, Revlimid, Temozolomide, Teniposide, Thioguanine, Valrubicin, Vinblastine, Vincristine, Vindesine and Vinorelbine.

In a further embodiment, the provided compositions are to be administered simultaneously or sequentially.

In a further aspect, the present invention relates to a method of treating a clinical condition characterized by expression of PDL2 (SEQ ID NO 1), the method comprising administering to an individual suffering from said clinical condition an effective amount of the peptide compound or fragment of the present invention or the nucleic acid of the present invention or vector of the present invention or host cell of the present invention.

In a still further aspect, the present invention relates to a method of treating or preventing cancer in a patient, the method comprising administering to the cancer patient an effective amount of the peptide compound or fragment of the present invention or the nucleic acid of the present invention or vector of the present invention or host cell of the present invention.

In a further aspect, the present invention relates to use of the peptide compound or fragment of the present invention or the nucleic acid of the present invention or vector of the present invention or host cell of the present invention for the manufacture of a medicament, such as an composition or vaccine, for the treatment or prevention of a cancer, such as cancer characterized by expression of PDL2.

In a still further aspect, the present invention relates to the peptide fragment of the present invention or the nucleic acid of the present invention or vector of the present invention or host cell of the present invention, for use in a method for treatment or prevention of a cancer, when administered simultaneously or sequentially with an additional cancer therapy, such as a cytokine therapy, a T-cell therapy, an NK therapy, an immune system checkpoint inhibitor, chemotherapy, radiotherapy, immunostimulating substances, gene therapy, antibodies and dendritic cells.

In an embodiment, the additional cancer therapy is selected from checkpoint blocking antibodies.

In a further embodiment the additional cancer therapy is selected from one or more of Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Nivolumab, Oxaliplatin, Paclitaxel, Pembrolizumab, Pemetrexed, Revlimid, Temozolomide, Teniposide, Thioguanine, Valrubicin, Vinblastine, Vincristine, Vindesine and Vinorelbine.

Further aspect are:

1. A peptide compound of PDL2 selected from:
   a) a peptide fragment of SEQ ID NO 1 consisting of a consecutive sequence of from 8 to 272 amino acids,
   b) a functional homologue having at least 70%, 80%, 90%, or 95% identity to SEQ ID NO 1 or the peptide fragment of a), and
   c) a functional analogue wherein at least one amino acid has been deleted, inserted and/or substituted in SEQ ID NO 1 or the peptide fragment of a),
   and wherein the C-terminal amino acid of any one of a), b) or c) also comprises the amide; or a pharmaceutically acceptable salt thereof 2. The peptide compound of aspect 1 selected from a) a peptide fragment of SEQ ID NO 1 consisting of a consecutive sequence of from 8 to 272 amino acids, wherein the C-terminal amino acid also comprises the amide;
   or a pharmaceutically acceptable salt thereof 3. The peptide compound of aspect 2 wherein the peptide fragment consists of a consecutive sequence in the range of from 8 to 250 amino acids, 8 to 200 amino acids, 8 to 150 amino acids, 8 to 120 amino acids, e.g. 10 to 100 amino acids, 20 to 80 amino acids, 30 to 60 amino acids, 40 to 50 amino acids.

4. The peptide compound of any one of aspects 2-3 wherein the peptide fragment of SEQ ID NO 1 is selected from the group consisting of PDL2(1-25), PDL2(1-50), PDL2(200-273), and PDL2(210-250).

5. The peptide compound of any one of aspects 2-4 wherein the consecutive sequence comprises one or more sequences selected from any one of SEQ ID NO 2-12, such as one sequence selected from SEQ ID NO 7 or two sequence selected from SEQ ID NO 2 and 4.

6. The peptide compound of any one of aspects 1-5 wherein the peptide fragment under a), the functional homologue under b), or the functional analogue under c) is capable of activating T-cells, such as CD4 and CD8 T-cells.

7. The peptide compound of aspect 6 wherein the activation is determined by the ELISPOT assay described herein.

8. A nucleic acid, such as DNA or RNA, encoding the peptide compound of any one of the preceding aspects.

9. A vector, such virus vector, comprising the nucleic acid of aspect 8.

10. A host cell, such as mammalian cell, comprising the vector of aspect 9.

11. A composition comprising the peptide compound of any one of aspects 1-7 or the nucleic acid of aspect 8 or the vector of aspect 9 or the host cell of aspect 10, optionally together with a pharmaceutically acceptable additive, such as carrier or adjuvant.

12. An immunotherapeutic composition comprising
    a) the peptide compound of any one of aspects 1-7 or the nucleic acid of aspect 8 or the vector of aspect 9 or the host cell of aspect 10; and
    b) an adjuvant;
    for use as a medicament.

13. The immunotherapeutic composition of aspect 12 for use in a method for treatment or prevention of a disease, disorder or condition selected from cancer, such as a tumor forming cancer disease.

14. The immunotherapeutic composition of any one of aspects 11-13 wherein the adjuvant is selected from the group consisting of bacterial DNA based adjuvants, oil/surfactant based adjuvants, viral dsRNA based adjuvants, imidazoquinolines, a Montanide ISA adjuvant.

15. A kit-of-parts comprising;
    a) the immunotherapeutic composition of any one of aspects 12-14, and
    b) a composition comprising at least one second active ingredient, selected from an immunostimulating compound, such as an interleukin, e.g. IL-2 and or IL-21, an anti-cancer agent, such as a chemotherapeutic agent, e.g. Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, nivolumab, Oxaliplatin, Paclitaxel, pembrolizumab, Pemetrexed, Revlimid, Temozolomide, Teniposide, Thioguanine, Valrubicin, Vinblastine, Vincristine, Vindesine and Vinorelbine.

16. The kits-of-parts according to aspect 15, where the provided compositions are to be administered simultaneously or sequentially.

17. A method of treating a clinical condition characterized by expression of PDL2 of SEQ ID NO 1, the method comprising administering to an individual suffering from said clinical condition an effective amount of the peptide compound of any one of aspects 1-7 or the nucleic acid of aspect 8 or vector of aspect 9 or host cell of aspect 10.

18. A method of treating or preventing cancer in a patient, the method comprising administering to the cancer patient an effective amount of the peptide compound of any one of aspects 1-7 or the nucleic acid of aspect 8 or vector of aspect 9 or host cell of aspect 10.

19. Use of the peptide compound of any one of aspects 1-7 or the nucleic acid of aspect 8 or vector of aspect 9 or host cell of aspect 10 for the manufacture of a medicament, such as an immunotherapeutic composition or vaccine, for the treatment or prevention of a cancer characterized by expression of PDL2.

20. A peptide compound of any one of aspects 1-7 or the nucleic acid of aspect 8 or vector of aspect 9 or host cell of aspect 10, for use in a method for treatment or prevention of a cancer, when administered simultaneously or sequentially with an additional cancer therapy, such as a cytokine therapy, a T-cell therapy, an NK therapy, an immune system checkpoint inhibitor, chemotherapy, radiotherapy, immunostimulating substances, gene therapy, antibodies and dendritic cells.

21. The peptide fragment, nucleic acid, vector or host cell of aspect 20 wherein the checkpoint blocking antibodies are selected from Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Nivolumab, Oxaliplatin, Paclitaxel, Pembrolizumab, Pemetrexed, Revlimid, Temozolomide, Teniposide, Thioguanine, Valrubicin, Vinblastine, Vincristine, Vindesine and Vinorelbine.

DETAILED DESCRIPTION OF THE INVENTION

Figure 1:
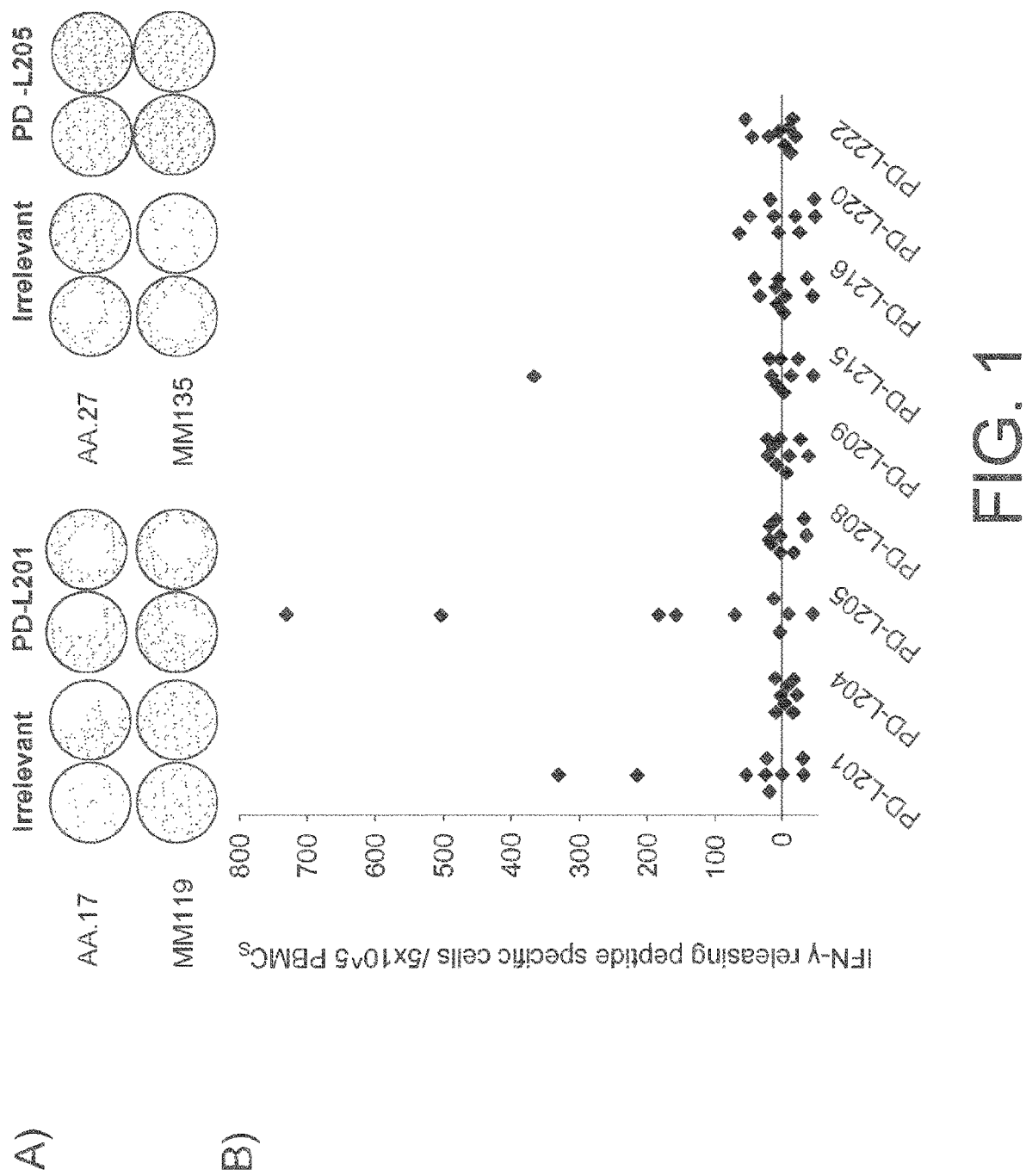
FIG. 1. Native T-cell responses to PD-L2. (A) Examples of ELISPOT results for PBMCs isolated from patients with malignant melanoma (AA and MM), in response to PD-L201 (PD-L2(4-12); LLLMLSLEL, SEQ ID NO: 2) and PD-L205 (PD-L2(16-25); QIAALFTVTV, SEQ ID NO: 4). (B) In-vitro IFN-γ ELISPOT results. PBMCs from 9 patients with cancer were stimulated once in vitro with each peptide. Then, the PBMCs were exposed to the peptides, and IFN-γ secretion was measured with ELISPOT. The response was calculated as the number of peptide-specific spots, minus the number of spots that reacted to an irrelevant peptide (HIV/HLA-A2; pol476-484; ILKEPVHGV, SEQ ID NO: 26), per $5 \times 10^5$ PBMCs.

In addition to the new immunogenic epitopes from PDL2 (SEQ ID NO 1), and strong immune responses against the new immunogenic epitopes as well as frequent immune responses detected against several peptide fragments of SEQ ID NO 1, the present inventor investigated different PD-L2-derived epitopes that might elicit T cell reactivity, and tested spontaneous T-cell mediated reactivity against PD-L2 in samples from both healthy donors and patients with different cancers. Finally, it was determined whether PD-L2-specific T cells could recognize target cells expressing PD-L2.

Regulatory feedback mechanisms, such as the upregulation of PD-L1 and PD-L2, are essential for limiting the strength and magnitude of immune responses that might otherwise harm the host. However, immune evasion is detrimental in the framework of cancer immunotherapy.

In one aspect, the present invention concerns a peptide compound of PDL2 selected from:
a) a peptide fragment of SEQ ID NO 1 consisting of a consecutive sequence of from 8 to 272 amino acids,
b) a functional homologue having at least 70%, 80%, 90%, or 95% identity to SEQ ID NO 1 or the peptide fragment of a), and
c) a functional analogue wherein at least one amino acid has been deleted, inserted and/or substituted in SEQ ID NO 1 or the peptide fragment of a),
and wherein the C-terminal amino acid of any one of a), b) or c) also comprises the amide; or a pharmaceutically acceptable salt thereof.

In the above-mentioned context, "functional" means "capable of stimulating an immune response to the PDL2 having SEQ ID NO: 1".

In another aspect the present invention concerns a peptide fragment of a human PDL2 protein of SEQ ID NO: 1, which fragment is up to 100 amino acids in length and wherein the peptide fragment comprises or consists of a consecutive sequence in a range from 8 to 100 amino acids of SEQ ID NO: 1,
or a pharmaceutically acceptable salt thereof.

In an embodiment the peptide fragment comprises or consists of a consecutive sequence in the range from 10 to 100 amino acids, such as from 10-17 amino acids, 20 to 30 amino acids, 30 to 40 amino acids, or from 40 to 50 amino acids.

In another embodiment the peptide fragment consists of a consecutive sequence in the range from 10 to 100 amino acids, such as from 10 to 17 amino acids, 20 to 30 amino acids, 30 to 40 amino acids, or from 40 to 50 amino acids. In an embodiment the peptide fragment is up to 60 amino acids in length, such as up to 50 amino acids, up to 40 amino acids, or up to 30 amino acids in length. The corresponding upper range in the consecutive sequence is accordingly, 60, 50, 40 or 30 amino acids of SEQ ID NO: 1.

In a further embodiment the peptide fragment is up to 21, 22, 23, 24, 25, 26, 27, 28, 29, or 30 amino acids in length.

In a further embodiment the consecutive sequence comprises one or more sequences selected from any one of SEQ ID NO 2, 4, 11 and 12. In a still further embodiment the consecutive sequence comprises the sequence SEQ ID NO 4. In a further embodiment the consecutive sequence consist of the sequence SEQ ID NO 4. In another embodiment the consecutive sequence comprises the sequence SEQ ID NO 11. In a further embodiment the consecutive sequence consist of the sequence SEQ ID NO 11. In another embodiment the consecutive sequence comprises the sequence SEQ ID NO 12. In a further embodiment the consecutive sequence consist of the sequence SEQ ID NO 12. In a further embodiment the consecutive sequence comprises both sequences SEQ ID NO 2 and SEQ ID NO 4.

In another embodiment the peptide fragment does not comprise amino acid 1-3 of SEQ ID NO 1, that is MIF. Thus, in an embodiment the peptide fragment comprises or consist of LLLMLSLELQLHQIAALFTVTV (SEQ ID NO: 25)

In a further embodiment the consecutive sequence comprises one or more sequences selected from any one of SEQ ID NO 2-12, such as any one of SEQ ID NO 2, 4, 11 and 12.

In a still further embodiment the consecutive sequence comprises both SEQ ID NO 2 and SEQ ID NO 4. For instance, the peptide fragment SEQ ID NO: 12 comprises both SEQ ID NO 2 and SEQ ID NO 4.

In a further embodiment the consecutive sequence comprises a sequence selected from SEQ ID NO 11, wherein the peptide fragment is up to 21, 22, 23, 24, 25, 26, 27, 28, 29, or 30 amino acids in length. Typically, 21 amino acids in length.

Thus, in a preferred aspect the present invention concerns a peptide fragment of a human PDL2 protein of SEQ ID NO: 1, which peptide fragment is up to 21, 22, 23, 24, 25, 26, 27, 28, 29, or 30 amino acids in length and wherein the peptide fragment comprises or consist of a sequence selected from SEQ ID NO 11; or a pharmaceutically acceptable salt thereof.

In a still further embodiment the consecutive sequence comprises a sequence selected from SEQ ID NO 12, wherein the peptide fragment is up to 25, 26, 27, 28, 29, or 30 amino acids in length.

In a further embodiment the consecutive sequence comprises a sequence selected from SEQ ID NO 4, wherein the peptide fragment is up to 10, 11, 12, 13, 14, 15, 16, 17, 18, 19, 20, 21, 22, 23, 24, 25, 26, 27, 28, 29, or 30 amino acids in length.

In a still further embodiment the consecutive sequence comprises a sequence selected from SEQ ID NO 2, wherein the peptide fragment is up to 9, 10, 11, 12, 13, 14, 15, 16, 17, 18, 19, 20, 21, 22, 23, 24, 25, 26, 27, 28, 29, or 30 amino acids in length.

In an embodiment, the peptide compound is selected from b) a functional homologue having at least 70%, 80%, 90%, or 95% identity to SEQ ID NO 1 or the peptide fragment of a), wherein the C-terminal amino acid also comprises the amide; or a pharmaceutically acceptable salt thereof. In one embodiment the functional homologue has at least 80% identity to SEQ ID NO 1. In a further embodiment the functional homologue has at least 90% identity to SEQ ID NO 1. In a further embodiment the functional homologue has at least 95% identity to SEQ ID NO 1. In a further embodiment the functional homologue has at least 70% identity to the peptide fragment of a). In a further embodiment the functional homologue has at least 80% identity to the peptide fragment of a). In a further embodiment the functional homologue has at least 90% identity to the peptide fragment of a). In a further embodiment the functional homologue has at least 95% identity to the peptide fragment of a).

In another embodiment the peptide compound is selected from c) a functional analogue wherein at least one amino acid has been deleted, inserted and/or substituted in SEQ ID NO 1 or the peptide fragment of a), wherein the C-terminal amino acid also comprises the amide; or a pharmaceutically acceptable salt thereof.

In a further embodiment, the peptide compound is selected from a) a peptide fragment of SEQ ID NO 1 consisting of a consecutive sequence of from 8 to 272 amino acids, wherein the C-terminal amino acid also comprises the amide; or a pharmaceutically acceptable salt thereof. In a further embodiment, the peptide fragment consists of a consecutive sequence in the range of from 8 to 250 amino acids. In a still further embodiment, the peptide fragment consists of a consecutive sequence in the range of from 8 to 200 amino acids. In a further embodiment, the peptide fragment consists of a consecutive sequence in the range of from 8 to 150 amino acids. In a still further embodiment, the peptide fragment consists of a consecutive sequence in the range of from 8 to 120 amino acids. In a further embodiment, the peptide fragment consists of a consecutive sequence in the range of from 10 to 100 amino acids. In a still further embodiment, the peptide fragment consists of a consecutive sequence in the range of from 20 to 80 amino acids. In a further embodiment, the peptide fragment consists of a consecutive sequence in the range of from 30 to 60 amino acids. In a still further embodiment, the peptide fragment consists of a consecutive sequence in the range of from 40 to 50 amino acids. In a further embodiment, the peptide fragment consists of a consecutive sequence in the range of from 8 to 30 amino acids. In a still further embodiment, the peptide fragment consists of a consecutive sequence in the range of from 10 to 25 amino acids. In a further embodiment, the peptide fragment consists of a consecutive sequence in the range of from 8 to 25 amino acids.

In a still further embodiment the peptide fragment of SEQ ID NO 1 is selected from the group consisting of PDL2(1-25), PDL2(1-50), PDL2(1-150), PDL2(1-200), PDL2(50-100), PDL2(50-150), PDL2(50-200), PDL2(60-100), PDL2(60-150), PDL2(60-200), PDL2(70-100), PDL2(70-150), PDL2(70-200), PDL2(200-273), and PDL2(210-250). In a preferred embodiment, the peptide fragment of SEQ ID NO 1 is selected from PDL2(1-25). In another preferred embodiment, the peptide fragment of SEQ ID NO 1 is selected from PDL2(1-50). In a further preferred embodiment, the peptide fragment of SEQ ID NO 1 is selected from PDL2(200-273). In a preferred embodiment, the peptide fragment of SEQ ID NO 1 is selected from PDL2(210-250).

In a further embodiment, the consecutive sequence comprises one or more sequences selected from any one of SEQ ID NO 2-24, such as one sequence selected from SEQ ID NO 7 or two sequence selected from SEQ ID NO 2 and 4. In a preferred embodiment, the consecutive sequence is selected from SEQ ID NO 4. In a preferred embodiment, the consecutive sequence is selected from SEQ ID NO 2. In a preferred embodiment, the consecutive sequence is selected from SEQ ID NO 7.

It is to be understood that when the peptide fragment consists of a consecutive sequence in the range of from 8 to 120, it may at the same time be selected within the sequence of for instance PDL2(1-150), whereas a peptide fragment consisting of a consecutive sequence in the range of from 8 to 272, cannot be at the same time be selected within the sequence of for instance PDL2(1-150), this is known to the person skilled in the art. Otherwise all combinations are contemplated within the present invention.

It is also to be understood that PDL2(x-y), wherein x and y are integers selected from 1-273 as used herein means a peptide fragment of human extended PDL2 having the SEQ ID NO 1 as defined herein, wherein x is the N-terminal amino acid and y is the C-terminal amino acid, for instance PDL2(16-25) indicates the peptide fragment from amino acid 16 of SEQ ID NO 1 to amino acid 25 of SEQ ID NO 1 wherein amino acid 16 is Q and amino acid 25 is V.

In any peptide fragment described herein, the C terminal amino acid may optionally be replaced with the corresponding amide, to improve solubility and/or to aid with manufacture/isolation. Similarly, the polypeptide may have attached at the N and/or C terminus at least one additional moiety to improve solubility and/or to aid with manufacture/isolation. Suitable moieties include hydrophilic amino acids. For example, the amino acids KR may be added at the N terminus and/or the amino acids RK may be added in order at the C terminus.

In a further aspect the present invention relates to a composition comprising a peptide fragment of a human PDL2 protein of SEQ ID NO: 1, which fragment is up to 100 amino acids in length and wherein the peptide fragment comprises or consists of a consecutive sequence in a range from 8 to 100 amino acids of SEQ ID NO: 1, or a pharmaceutically acceptable salt thereof; optionally together with a pharmaceutically acceptable additive, such as a carrier or adjuvant.

The term "identity" as used herein refers to a relationship between the sequences of two or more peptides, such as polypeptides, as determined by comparing the sequences. In the art, "identity" also means the degree of sequence relatedness between proteins or polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related proteins or peptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math., 48, 1073, (1988).

Preferred methods to determine identity are designed to give the largest match between the sequences tested. Methods to determine identity are described in publicly available computer programs. Preferred computer program methods to determine identity between two sequences include the GCG program package, including GAP (Devereux et al., Nucl. Acid. Res., 12, 387, (1984); Genetics Computer Group, University of Wisconsin, Madison, Wis.), BLASTP, BLASTN, and FASTA (Altschul et al., J. Mol. Biol., 215, 403-410, (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

For example, using the computer algorithm GAP (Genetics Computer Group, University of Wisconsin, Madison, Wis.), two proteins for which the percent sequence identity is to be determined are aligned for optimal matching of their respective amino acids (the "matched span", as determined by the algorithm). A gap opening penalty (which is calculated as 3 times the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp. 3 (1978) for the PAM 250 comparison matrix; Henikoff et al., Proc. Natl. Acad. Sci USA, 89, 10915-10919, (1992) for the BLOSUM 62 comparison matrix) is also used by the algorithm. Preferred parameters for a protein or peptide sequence comparison include the following: Algorithm: Needleman et al., J. Mol. Biol, 48, 443-453, (1970); Comparison matrix: BLOSUM 62 from Henikoff et al., Proc. Natl. Acad. Sci. USA, 89, 10915-10919, (1992); Gap Penalty: 12, Gap Length Penalty: 4, Threshold of Similarity: 0. The GAP program is useful with the above parameters. The aforementioned parameters are the default parameters for protein comparisons (along with no penalty for end gaps) using the GAP algorithm.

In a still further embodiment the peptide fragment under a), the functional homologue under b), or the functional analogue under c) is capable of activating T-cells, such as CD4 and CD8 T-cells. Typically, the activation is determined by the ELISPOT assay described herein.

In a further embodiment, the peptide fragment under a) is capable of activating T-cells as determined by the ELISPOT assay described herein.

In a further aspect the present invention relates to a nucleic acid encoding the peptide compound of the present invention. The peptide compound of the present invention is selected from any one of the above embodiments. In one embodiment the nucleic acid is selected from the group consisting of DNA and RNA.

In a still further aspect the present invention relates to a vector comprising the nucleic acid of the present invention. The nucleic acid of the present invention is selected from any one of the above embodiments, and the peptide compound of the present invention is selected from any one of the above embodiments. In one embodiment the vector is selected from a virus vector.

In a further aspect the present invention relates to a host cell comprising the vector of the present invention. The vector of the present invention is selected from any one of the above embodiments, the nucleic acid of the present invention is selected from any one of the above embodiments, and the peptide compound of the present invention is selected from any one of the above embodiments. In one embodiment the host cell is selected from a mammalian cell.

In a still further aspect the present invention relates to a composition comprising the peptide compound or fragment of the present invention or the nucleic acid of the present invention or the vector of the present invention or the host cell of the present invention, optionally together with a pharmaceutically acceptable additive, such as carrier or adjuvant.

In a still further aspect the present invention relates to a composition comprising
  a) the peptide compound or fragment of the present invention or the nucleic acid of the present invention or the vector of the present invention or the host cell of the present invention; and
  b) an adjuvant;
  for use as a medicament.

In an embodiment the composition of the present invention is for use in a method for treatment or prevention of a disease, disorder or condition selected from cancer. In one embodiment the cancer is a tumor forming cancer disease. In a further embodiment the cancer is selected from any one of melanoma, renal cell carcinoma, non-hodgkin lymphoma, and ovarian cancer. In a further embodiment the adjuvant is selected from the group consisting of bacterial DNA based adjuvants, oil/surfactant based adjuvants, viral dsRNA based adjuvants, imidazoquinolines, and a Montanide ISA adjuvant.

In a further aspect the present invention relates to a kit-of-parts comprising;
  a) the composition of the present invention, and
  b) a composition comprising at least one second active ingredient, selected from an immunostimulating compound, such as an interleukin, e.g. IL-2 and or IL-21, an anti-cancer agent, such as a chemotherapeutic agent, e.g. Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, nivolumab, Oxaliplatin, Paclitaxel, pembrolizumab, Pemetrexed, Revlimid, Temozolomide, Teniposide, Thioguanine, Valrubicin, Vinblastine, Vincristine, Vindesine and Vinorelbine.

In an embodiment of the kits-of-parts, the provided compositions are to be administered simultaneously or sequentially.

In a further aspect, the present invention relates to a method of treating a clinical condition characterized by expression of PDL2 of SEQ ID NO 1, the method comprising administering to an individual suffering from said clinical condition an effective amount of the peptide compound of the present invention or the nucleic acid of the present invention or the vector of the present invention or the host cell of the present invention.

In a still further aspect the present invention relates to use of the peptide compound of the present invention, or the nucleic acid of the present invention, or the vector of the present invention, or the host cell of the present invention, for the manufacture of a medicament, such as an composition or vaccine, for the treatment or prevention of a cancer characterized by expression of PDL2.

In a further aspect, the present invention relates to the peptide compound of the present invention, or the nucleic acid of the present invention, or the vector of the present invention, or the host cell of the present invention, for use in a method for treatment or prevention of a cancer, when administered simultaneously or sequentially with an additional cancer therapy.

In an embodiment the additional cancer therapy is selected from the group consisting of a cytokine therapy, a T-cell therapy, an NK therapy, an immune system checkpoint inhibitor, chemotherapy, radiotherapy, immunostimulating substances, gene therapy, anti-bodies and dendritic cells. In one embodiment the additional cancer therapy is selected from an immune system checkpoint inhibitor. In a particular embodiment, the immune system checkpoint inhibitor is a checkpoint blocking antibody. In a further embodiment the additional cancer therapy is selected from the group consisting of Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Nivolumab, Oxaliplatin, Paclitaxel, Pembrolizumab, Pemetrexed, Revlimid, Temozolomide, Teniposide, Thioguanine, Valrubicin, Vinblastine, Vincristine, Vindesine and Vinorelbine.

As used herein any amino acid sequence shown may be modified at the C-terminal amino acid to be on amide form (—CONH$_2$) or may be on acid form (—COOH), thus any one of these are preferred embodiments, and it is intended that any C-terminal amino acid, such as I, L, V, comprises both amide and acid form unless specified by —NH2 or —OH.

The PDL2 peptide fragments disclosed herein are made by standard peptide synthesis, such as solid-phase peptide synthesis (SPPS). SPPS is a standard method for synthesizing peptides in the lab. SPPS allows for the synthesis of natural peptides which are difficult to express in bacteria, the incorporation of unnatural amino acids, peptide/protein backbone modification, and the synthesis of D-proteins, which consist of D-amino acids. Small porous beads are treated with functional units ('linkers') on which peptide chains can be built. The peptide will remain covalently attached to the bead until cleaved from it by a reagent such as anhydrous hydrogen fluoride or trifluoroacetic acid. The peptide is thus 'immobilized' on the solid-phase and can be retained during a filtration process while liquid-phase reagents and by-products of synthesis are flushed away. The general principle of SPPS is one of repeated cycles of deprotection-wash-coupling-wash. The free N-terminal amine of a solid-phase attached peptide is coupled to a single N-protected amino acid unit. This unit is then deprotected, revealing a new N-terminal amine to which a further amino acid may be attached. The superiority of this technique partially lies in the ability to perform wash cycles after each reaction, removing excess reagent with all of the growing peptide of interest remaining covalently attached to the insoluble resin. There are two majorly used forms of SPPS—Fmoc and Boc. Unlike ribosome protein synthesis, solid-phase peptide synthesis proceeds in a C-terminal to N-terminal fashion. The N-termini of amino acid monomers is protected by either of these two groups and added onto a deprotected amino acid chain. Automated synthesizers are available for both techniques, though many research groups continue to perform SPPS manually. Furthermore, the skilled person will understand that the processes described above and hereinafter the functional groups of intermediate compounds may need to be protected by protecting group.

When the peptide compounds, nucleic acids, vectors, host cells and pharmaceutical compositions herein disclosed are used for the above treatment, a therapeutically effective amount of at least one compound is administered to a mammal in need of said treatment.

As used herein amino acids are identified by the one or three letter code known to the person skilled in the art and shown in the table below for convenience:

Amino Acids, One and Three Letter Codes

| Amino acid | Three letter code | One letter code |
|---|---|---|
| alanine | ala | A |
| arginine | arg | R |
| asparagine | asn | N |
| aspartic acid | asp | D |
| asparagine or aspartic acid | asx | B |
| cysteine | cys | C |
| glutamic acid | glu | E |
| glutamine | gln | Q |
| glutamine or glutamic acid | glx | Z |
| glycine | gly | G |
| histidine | his | H |
| isoleucine | ile | I |
| leucine | leu | L |
| lysine | lys | K |
| methionine | met | M |
| phenylalanine | phe | F |
| proline | pro | P |
| serine | ser | S |
| threonine | thr | T |
| tryptophan | trp | W |
| tyrosine | tyr | Y |
| valine | val | V |

The term "immunogenic" as used herein means that a peptide fragment is capable of eliciting an immune response, preferably a T-cell response, in at least one individual after administration to said individual. A polypeptide may be identified as immunogenic using any suitable method, including in vitro methods. For example, a peptide may be identified as immunogenic if it has at least one of the following characteristics:
   (i) It is capable of eliciting IFN-γ-producing cells in a PBL population of at least one cancer patient as determined by an ELISPOT assay, and/or
   (ii) It is capable of in situ detection in a sample of tumor tissue of CTLs that are reactive with the corresponding PDL2; and/or
   (iii) It is capable of inducing the in vitro growth of specific T-cells.

Methods suitable for determining whether a polypeptide is immunogenic active are also provided in the Examples section below.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The treatment may either be performed in an acute or in a chronic way. The patient to be treated is preferably a mammal; in particular a human being, but it may also include animals, such as dogs, cats, cows, monkeys, apes, sheep and pigs.

The term "a therapeutically effective amount" of a peptide compound of the present invention or a peptide fragment disclosed herein, as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In a still further aspect the present invention relates to a pharmaceutical composition comprising the peptide compound, such as peptide fragment, of the present invention and optionally a pharmaceutically acceptable additive, such as a carrier or an excipient.

As used herein "pharmaceutically acceptable additive" is intended without limitation to include carriers, excipients, diluents, adjuvant, colorings, aroma, preservatives etc. that the skilled person would consider using when formulating a compound of the present invention in order to make a pharmaceutical composition.

The adjuvants, diluents, excipients and/or carriers that may be used in the composition of the invention must be pharmaceutically acceptable in the sense of being compatible with the peptide compound, peptide fragment, nucleic acid, vector, or host cell and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person within the art.

Adjuvants are any substance whose admixture into the composition increases or otherwise modifies the immune response elicited by the composition. Adjuvants, broadly defined, are substances which promote immune responses. Adjuvants may also preferably have a depot effect, in that they also result in a slow and sustained release of an active agent from the administration site. A general discussion of adjuvants is provided in Goding, Monoclonal Antibodies: Principles & Practice (2nd edition, 1986) at pages 61-63.

Adjuvants may be selected from the group consisting of: AlK(SO4)2, AlNa(SO4)2, AlNH4 (SO4), silica, alum, Al(OH)3, Ca3 (PO4)2, kaolin, carbon, aluminum hydroxide, muramyl dipeptides, N-acetyl-muramyl-L-threonyl-D-isoglutamine (thr-DMP), N-acetylnormuramyl-L-alanyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxphosphoryloxy)-ethylamine (CGP 19835A, also referred to as MTP-PE), RIBI (MPL+TDM+CWS) in a 2% squalene/Tween-80® emulsion, lipopolysaccharides and its various derivatives, including lipid A, Freund's Complete Adjuvant (FCA), Freund's Incomplete Adjuvants, Merck Adjuvant 65, polynucleotides (for example, poly IC and poly AU acids), wax D from Mycobacterium, tuberculosis, substances found in *Corynebacterium parvum, Bordetella pertussis*, and members of the genus *Brucella*, Titermax, ISCOMS, Quil A, ALUN (see U.S. Pat. Nos. 58,767 and 5,554,372), Lipid A derivatives, choleratoxin derivatives, HSP derivatives, LPS derivatives, synthetic peptide matrixes or GMDP, Interleukin 1, Interleukin 2, Montanide ISA-51 and QS-21. Various saponin extracts have also been suggested to be useful as adjuvants in immunogenic compositions. Granulocyte-macrophage colony stimulating factor (GM-CSF) may also be used as an adjuvant.

Preferred adjuvants to be used with the invention include oil/surfactant based adjuvants such as Montanide adjuvants (available from Seppic, Belgium), preferably Montanide ISA-51. Other preferred adjuvants are bacterial DNA based adjuvants, such as adjuvants including CpG oligonucleotide sequences. Yet other preferred adjuvants are viral dsRNA based adjuvants, such as poly I:C. GM-CSF and Imidazoquinolines are also examples of preferred adjuvants.

The adjuvant is most preferably a Montanide ISA adjuvant. The Montanide ISA adjuvant is preferably Montanide ISA 51 or Montanide ISA 720.

In Goding, Monoclonal Antibodies: Principles & Practice (2nd edition, 1986) at pages 61-63 it is also noted that, when an antigen of interest is of low molecular weight, or is poorly immunogenic, coupling to an immunogenic carrier is recommended. A peptide compound, peptide fragment, nucleic acid, vector, or host cell of an composition of the invention may be coupled to a carrier. A carrier may be present independently of an adjuvant. The function of a carrier can be, for example, to increase the molecular weight of the peptide compound, peptide fragment, nucleic acid, vector, or host cell in order to increase activity or immunogenicity, to confer stability, to increase the biological activity, or to increase serum half-life. Furthermore, a carrier may aid in presenting the polypeptide or fragment thereof to T-cells. Thus, in the immunogenic composition, the polypeptide or fragment thereof may be associated with a carrier, such as those set out below.

The carrier may be any suitable carrier known to a person skilled in the art, for example a protein or an antigen presenting cell, such as a dendritic cell (DC). Carrier proteins include keyhole limpet hemocyanin, serum proteins such as transferrin, bovine serum albumin, human serum albumin, thyroglobulin or ovalbumin, immunoglobulins, or hormones, such as insulin or palmitic acid. Alternatively, the carrier protein may be tetanus toxoid or diphtheria toxoid. Alternatively, the carrier may be a dextran such as sepharose. The carrier must be physiologically acceptable to humans and safe.

The composition may optionally comprise a pharmaceutically acceptable excipient. The excipient must be 'acceptable' in the sense of being compatible with the other ingredients of the composition and not deleterious to the recipient thereof. Auxiliary substances, such as wetting or emulsifying agents, pH buffering substances and the like, may be present in the excipient. These excipients and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

The composition may be prepared, packaged, or sold in a form suitable for bolus administration or for continuous administration. Injectable compositions may be prepared, packaged, or sold in unit dosage form, such as in ampoules or in multi-dose containers containing a preservative. Compositions include, but are not limited to, suspensions, solutions, emulsions in oily or aqueous vehicles, pastes, and implantable sustained-release or biodegradable formulations. In one embodiment of a composition, the active ingredient is provided in dry (for e.g., a powder or granules) form for reconstitution with a suitable vehicle (e. g., sterile pyrogen-free water) prior to administration of the reconstituted composition. The composition may be prepared, packaged, or sold in the form of a sterile injectable aqueous or oily suspension or solution. This suspension or solution may be formulated according to the known art, and may comprise, in addition to the active ingredient, additional ingredients such as the adjuvants, excipients and auxiliary substances described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Other compositions which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt. Alternatively, the active ingredients of the composition may be encapsulated, adsorbed to, or associated with, particulate carriers. Suitable particulate carriers include those derived from polymethyl methacrylate polymers, as well as PLG microparticles derived from poly (lactides) and poly(lactide-co-glycolides). See, e.g., Jeffery et al. (1993) Pharm. Res. 10:362-368. Other particulate systems and polymers can also be used, for example, polymers such as polylysine, polyarginine, polyornithine, spermine, spermidine, as well as conjugates of these molecules.

As mentioned above, the compositions and particularly immunotherapetic compositions as herein disclosed may, in addition to the compounds herein disclosed, further comprise at least one pharmaceutically acceptable adjuvant, diluent, excipient and/or carrier. In some embodiments, the pharmaceutical compositions comprise from 1 to 99 weight % of said at least one pharmaceutically acceptable adjuvant, diluent, excipient and/or carrier and from 1 to 99 weight % of a compound as herein disclosed. The combined amount of the active ingredient and of the pharmaceutically acceptable adjuvant, diluent, excipient and/or carrier may not constitute more than 100% by weight of the composition, particularly the pharmaceutical composition.

In some embodiments, only one compound or peptide as herein disclosed is used for the purposes discussed above.

In some embodiments, two or more of the compound as herein disclosed are used in combination for the purposes discussed above.

The composition, particularly immunotherapeutic composition comprising a compound set forth herein may be adapted for oral, intravenous, topical, intraperitoneal, nasal, buccal, sublingual, or subcutaneous administration, or for administration via the respiratory tract in the form of, for example, an aerosol or an air-suspended fine powder. Therefore, the pharmaceutical composition may be in the form of, for example, tablets, capsules, powders, nanoparticles, crystals, amorphous substances, solutions, transdermal patches or suppositories.

Further embodiments of the process are described in the experimental section herein, and each individual process as well as each starting material constitutes embodiments that may form part of embodiments.

The above embodiments should be seen as referring to any one of the aspects (such as 'method for treatment', 'composition', 'peptide compound for use as a medicament', or 'peptide compound for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present invention is further illustrated by the following examples that, however, are not to be construed as limiting the scope of protection. The features disclosed in the foregoing description and in the following examples may, both separately and in any combination thereof, be material for realizing the invention in diverse forms thereof.

Experimental

Patients, Protocols, Methods and Discussion

Patient Material

We collected blood samples from patients with melanoma, renal cell carcinoma, non-hodgkin lymphoma, and ovarian cancer and from healthy. Samples were collected a minimum of four weeks after the termination of any kind of anti-cancer therapy. Peripheral blood mononuclear cells (PBMCs) were isolated using Lymphoprep™ (Alere A S, cat. 1114547) separation, HLA-typed and frozen in FCS with 10% DMSO (Sigma-Aldrich, cat. D5879-100ML). Tumor Infiltrating lymphocytes (TIL) from lesions from two melanoma patients were expanded using high dose IL-2 (6000 units/ml). The protocol was approved by the Scientific Ethics Committee for The Capital Region of Denmark and conducted in accordance with the provisions of the Declaration of Helsinki. Before study entry, a written informed consent from the patients was obtained.

Peptides

We identified 22 HLA-A2 restricted, 9-10 amino acid-long peptides in the human PD-L2 protein with an online epitope prediction database, SYFPEITHI (syfpeithi.de). Of these 22 peptides, we selected 9, from either the signal sequence or the transmembrane domain of PD-L2, and had them synthesized by TAG Copenhagen (Copenhagen, Denmark). These peptides were: PD-L201 (PD-L2(4-12); LLL-MLSLEL, SEQ ID NO: 2), PD-L204 (PD-L2(231-240); IIAFIFIATV, SEQ ID NO:3), PD-L205 (PD-L2(16-25); QIAALFTVTV, SEQ ID NO: 4), PD-L208 (PD-L2(6-14); LMLSLELQL, SEQ ID NO: 5), PD-L209 (PD-L2(9-17); SLELQLHQI, SEQ ID NO: 6), PD-L215 (PD-L2(234-243); FIFIATVIAL, SEQ ID NO: 7), PD-L216 (PD-L2(11-20); ELQLHQIAAL, SEQ ID NO:8), PD-L220 (PD-L2(1-10); MIFLLLMLSL, SEQ ID NO: 9), and PD-L222 (PD-L2 (226-235); FIPFCIIAFI, SEQ ID NO: 10). We also analyzed two peptides with 21-25 amino acids: PD-L2long1 (PD-L2 (9-29); SLELQLHQIAALFTVTVPKEL, SEQ ID NO: 11) and PD-L2long2 (PD-L2(1-25); MIFLLL-MLSLELQLHQIAALFTVTV, SEQ ID NO: 12). The HLA-A2 high affinity binding epitope, HIV-1 pol476-484 (ILKEPVHGV; SEQ ID NO 26), was used as an irrelevant control. A previously described PD-L1 peptide named as PD-L101 (PDL1(15-23); LLNAFTVTV; SEQ ID NO 27) was used in cross reactivity experiments (1). All peptides were dissolved in either DMSO or sterile water before the experiments.

ELISPOT Assay

The IFN-γ and TNF-α ELISPOT technique was performed as described previously (3). We performed the assays according to the guidelines provided by the cancer immunotherapy immunoguiding program (CIP; cimt.eu/cimt/files/dl/cip guidelines.pdf). Unless stated otherwise, PBMCs were stimulated once in vitro with peptide prior to analysis to extend the sensitivity of the assay. To measure T-cell reactivity, nitrocellulose-bottomed 96-well plates (MultiScreen MSIPN4W; Millipore) were coated overnight at room temperature or two days at 4° C. with the relevant antibodies. The wells were washed and blocked with X-vivo medium for 2 h. The PBMCs were added at different cell concentrations in triplicate wells, with PD-L2 peptide or with control peptide, and incubated overnight. The following day, the wells were washed, and the relevant biotinylated secondary antibody (Mabtech) was added, followed by the avidin-enzyme conjugate (AP-Avidin; Calbiochem/Invitrogen Life Technologies); finally, we added the enzyme substrate, NBT/BCIP (Invitrogen Life Technologies) for visualization. The spots on the developed ELISPOT plates were analyzed on a CTL ImmunoSpot S6 Ultimate-V analyzer with Immunospot software, v5.1.

Generation of PD-L2-Specific T-Cell Cultures

PBMCs from a patient with melanoma were stimulated with irradiated (30 Gy) autologous DCs, which had been pulsed with PD-L205 (PD-L2(16-25)) peptide (PBL:DC ratio 10:1) and IL-7 (40 U/ml) were added (PeproTech, London, UK). The next day, IL-12 (20 U/ml) was added (PeproTech, London, UK). At weekly intervals, we performed three identical stimulations, with irradiated autologous DCs loaded with PDL205 (PD-L2(16-25)), and IL-12 (20 U/ml) added the next day. Then, at weekly intervals, we stimulated the culture three more times with irradiated autologous PBLs loaded with PDL205 (PD-L2(16-25)) (culture:PBL ratio 1:1), but the next day, we added IL-2 (120 U/ml; Proleukin, Novartis).

The culture was enriched for specific T cells, either by staining with an anti-CD137-PE antibody (BD-Biosciences) or by employing a TNF-α-enrichment and detection kit (according to the procedure by Miltenyi Biotec). Next, we performed magnetic cell isolation with a MACs microbead column (according to the procedure by Miltenyi Biotec). The sorted cells were rapidly expanded by incubating with 0.6 µg anti-CD3 antibody (eBioscience, clone OKT3) and a high dose of IL-2 (Proleukin, Novartis).

Intracellular Cytokine Staining

To detect cell subpopulations that produced cytokines, we stimulated a PD-L1-specific T-cell culture (previously described (1)) and a PD-L2-specific T-cell culture with 5 µg/ml of relevant or irrelevant peptide, and incubated the cells for 5 h at 37° C. with 5% CO2. After 1 h of incubation, we added GolgiPlug (BD), diluted at 1:200. After 4 h, cells were washed twice with PBS, stained with fluorochrome-conjugated antibodies specific for surface markers (CD3-APC-H7, CD4-PerCP/FITC, CD8-Pacific Blue/PerCP, and Horizon Fixable Viability Stain 510, all from BD). Cells were washed, fixed, and permeabilized with Fixation/Permeabilization and Permeabilization Buffer (eBioscience), according to the manufacturer's instructions. Cells were subsequently stained with fluorochrome-conjugated antibodies to visualize intracellular cytokines. The following antibody-fluorochrome combinations were used: IFNγ-PE-CY7/APC (eBioscience) and TNFα-APC/BV421 (eBioscience). Relevant isotype controls were used to enable correct compensation and confirm antibody specificity. Stained cells were analyzed with a BD FACSCanto II flow cytometer. Analysis was performed with BD FACSDiva Software.

Cytotoxicity Assay PD-L1-specific and PD-L2-specific T-cell-mediated cytotoxicity was measured with conventional 51chromium-release assays, as previously described (4). Target cells were TAP deficient T2 cells, pulsed with HIV-1 pol476-484 (ILKEPVHGV, SEQ ID NO: 26), PD-L101 (PD-L1(15-23)), or PD-L205 (PD-L2(16-25)).

siRNA-Mediated PD-L2 Silencing of DCs

All Silencer® Select siRNA duplexes for targeted silencing of PD-L2 and Silencer® Select siRNA negative control duplex for medium GC content were obtained from Ambion® by Life Technology.

The PD-L2 siRNA duplexes consisted of three transcripts: 1. (sence) 5''-CAUCCUAAAGGUUCCAGAAtt-3' (SEQ ID NO 28), (antisense) 5'-UU CUGGAACCUUUAG-GAUGtg3' (SEQ ID NO 29)—(siRNA ID #s37285), 2. (sense) 5'-CCUAAGGAACUGUACAUAAtt-3' (SEQ ID NO 30), (antisense) 5'-UUAUGUACAGUUCCUUAGGga 3' (SEQ ID NO 31)—(siRNA ID #s37286) and 3. (sence) 5'-GAAAACAACUCUGUCAAAAtt-3' (SEQ ID NO 32), (antisense) 5'-UUUUGACAGAGUUGUUUUCtt 3' (SEQ ID NO 33)—(siRNA ID #s37287). The siRNA duplexes were dissolved in RNase-free water to a final concentration of 100 µM and subsequently stored at −80° C.

Autologous CD14+ monocytes were enriched using MACS CD14 MicroBeads (Miltenyi Biotech). The enriched monocytes were cultured using CellGro (CellGenix), and supplemented with GM-CSF (1000 U/ml) and IL-4 (250 U/ml) (both PeproTech). The next day, the cells were harvested and transfected with either PD-L2 siRNA or negative control siRNA. The transfection procedure and electroporation parameters were used as previously described (13) For electroporation, cells were resuspended at a concentration of 2×106 per 200 ul of Opti-MEM medium (Invitrogen). Cells were kept on ice and added with 0.25 nmol of each PD-L2 siRNA duplexes. Subsequently, cells were transferred into a 2 mm kuvette and were electroporated with a single pulse at 250 Volts for 2 milli seconds using a BTX 830 square-wave electroporator (Harvard Apparatus, Holliston MA, USA).

Immediately after electroporation, monocytes were transferred to prewarmed CellGro medium containing DC-maturation cocktail: IL-β (1,000 U/mL), IL-6 (1,000 U/mL), TNF-α (1,000 U/mL), and PGE2 (1 mg/mL) (all from PeproTech). After 48 hours incubation, the transfected matured DCs were used for experimental analysis. PD-L2 surface expression on the DCs transfected with PD-L2 siRNA and negative control siRNA was analyzed using anti-human PD-L2-PE (BD biosciences). Functionality of PD-L2-specific T-cell cultures towards transfected autologous DCs was analysed using ICS and ELISPOT assay as described above. For ICS, T-cell cultures were stimulated with either PD-L2 siRNA or negative control transfected DCs for 5 hours with ratio of 1:5. In EliSpot assay T-cell cultures were stimulated with the DCs for 24 hours with ratio of 1:5. Statistical analysis An ELISPOT response was defined, based on the guidelines and recommendations provided by CIP and Moodie et al (5). The non-parametric distribution-free resampling (DFR) and more conservative DFR×2 statistical test were used for a formal comparison between antigen-stimulated wells and negative-control wells. The ELISPOT assays were performed at least in triplicate.

Results

Natural T Cell Reactivity Against PD-L2

The amino acid sequence of the PD-L2 protein was screened with the "SYFPEITHI" database (15) to predict the best HLA-A2 peptide epitopes. The algorithm identified 22 peptides that were top candidates, based on predictive scores in the range of 22-29. We selected 9 peptides for synthesis and further study, based on their location in the PD-L2 protein. At least part of the peptide had to be located in the signal peptide or the transmembrane domain. These nine peptides were used with the IFN-γ ELISPOT in vitro assay to test for the presence of specific T-cell responses in PBMCs from different HLA-A2+ patients with cancer. We detected immune responses against PD-L215 (PD-L2(234-243)), and in particular, against PD-L201 (PD-L2(4-12)) and PD-L205 (PD-L2(16-25)) (FIG. 1).

Figure 2:
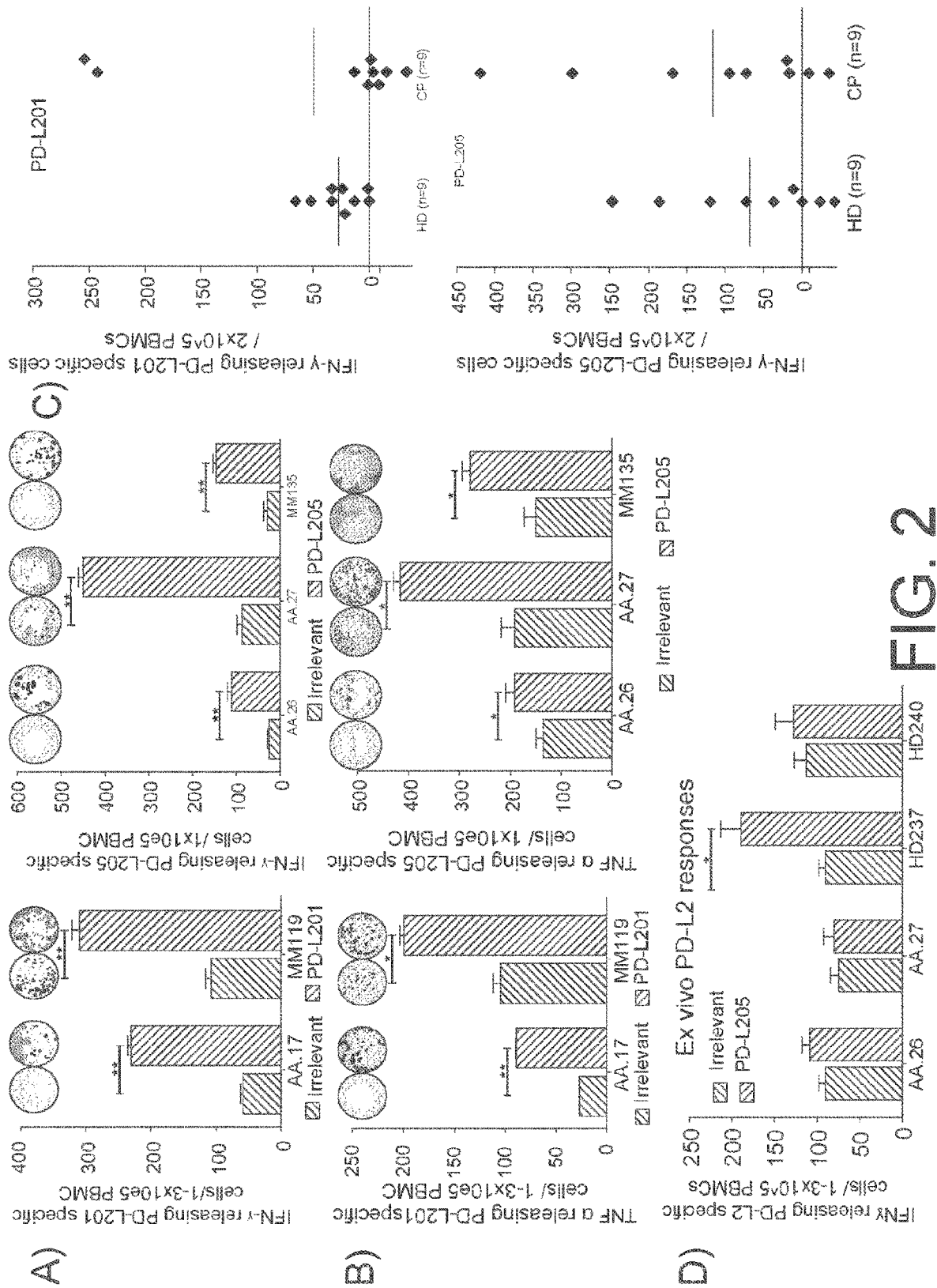
FIG. 2. PD-L2 elicited responses in T cells from patients with cancer and T cells from healthy donors. (A) Examples of IFN-γ responses against PD-L201 (PD-L2(4-12)) and PD-L205 (PD-L2(16-25))(black bars) or irrelevant peptide (grey bars) in PBMCs from patients with malignant melanoma (AA and MM). All experiments were performed in triplicate,  significant according to the DFR and DFR×2. (B) Examples of TNF-α responses against PD-L201 (PD-L2(4-12)) and PD-L205 (PD-L2(16-25)) (black bars) or irrelevant peptide (grey bars) in PBMCs from patients with malignant melanoma (AA and MM),  significant according to the DFR and DFR×2; * significant according to only the DFR. (C) In-vitro IFN-γ ELISPOT results. PBMCs from 9 patients with cancer and 9 healthy donors were stimulated once in vitro with PD-L201 (PD-L2(4-12)) or PD-L205 (PD-L2(16-25)). Then, PBMCs were exposed to the peptides, and IFN-γ secretion was measured with ELISPOT. The average number of peptide-specific spots (after subtracting the number of spots without added peptide) was calculated per $2-5 \times 10^5$ PBMCs. (D) Ex vivo IFN-γ ELISPOT results. PD-L205 (PD-L2(16-25)) (black bars) or the irrelevant peptide (grey bars) elicited responses in PBMCs from two patients with malignant melanoma (AA) and in PBMCs from two healthy donors (HD).

Next, we utilized both the IFN-γ and TNF-α ELISPOT assays to examine 5 selected PBMCs for immune responses against PD-L201 (PD-L2(4-12)) and PD-L205 (PD-L2(16-25)) (FIGS. 2A and 2B). All IFN-γ and TNF-α responses were statistically significant, according to the DFR test (FIGS. 2A and 2B). In addition, the IFN-γ responses and one TNF-α response were statistically significant according to the DFR×2 rule (FIGS. 2A and 2B). Next, we tested PBMCs from healthy donors for immune responses against both PD-L2-derived epitopes with the IFN-γ ELISPOT assay. We detected strong immune responses against PD-L205 (PD-L2(16-25)), and weaker responses against PD-L201 (PD-L2 (4-12)) in healthy individuals (FIG. 2C). In general, PD-L205 (PD-L2(16-25)) appeared to be the dominant epitope for eliciting immune responses. Next, we tested PBMCs from four donors, directly ex vivo (without prior in vitro peptide stimulation), for responses against PD-L205 (PD-L2(16-25)) with the IFN-γ ELISPOT assay (FIG. 2D). The PBMCs from one of these donors showed an ex vivo IFN-γ response that was statistically significant, according to the DFR rule (FIG. 2D).

Figure 3:
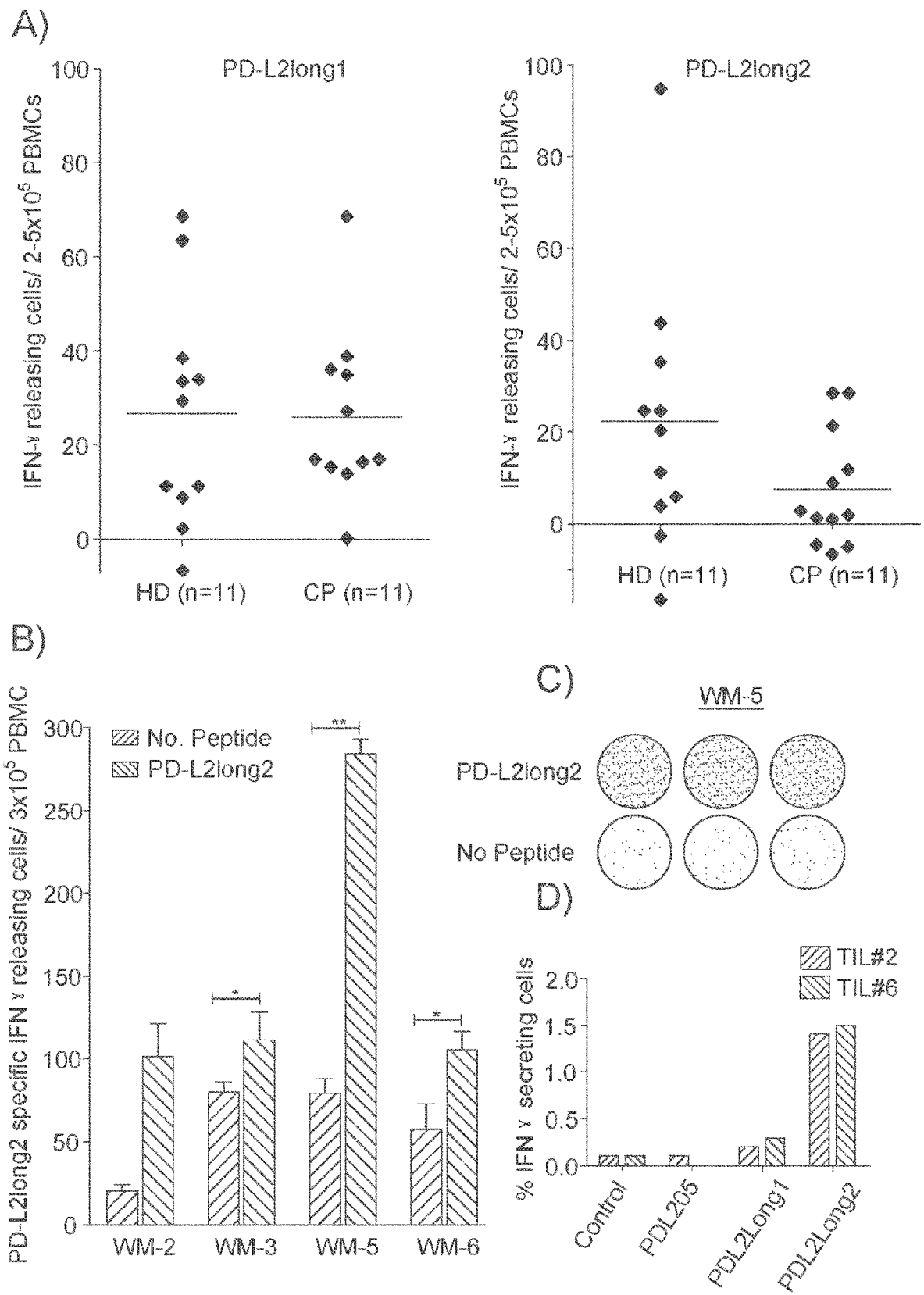
FIG. 3: Reactivity towards long PD-L2 peptides spanning the signal peptide part of the PD-L2 sequence. (A) In vitro IFN-γ ELISPOT results. PBMCs from 11 patients with malignant melanoma and 11 healthy donors were stimulated with PD-L2long1 (PD-L2(9-29); SLELQLHQIAALFTVTVPKEL, SEQ ID NO: 11) or PD-L2long2 (PD-L2(1-25); MIFLLLMLSLELQLHQIAALFTVTV, SEQ ID NO: 12) and screened for IFNγ responses, by measuring IFNγ release in an in vitro ELISPOT assay. (B) PBMCs from four non-hodgkin lymphoma patients (WM) screened for IFNγ responses towards PD-L2long2 (PD-L2(1-25)) in an in vitro ELISPOT assay. All assays were made in triplicates with $3*10^6$ cells per well, except one which were made in duplicates (WM-2). ** denotes as significant according to the DFR and DFR×2; * denotes significant according to only the DFR. (C) Examples of ELISPOT well images for WM-5 patient in response to PD-L2long2. (D) Intracellular cytokine staining of tumor infiltrating T-lymphocytes (TILs) from two melanoma patients (TIL2, black bars and TILE, white bars) shows CD4+ T cell release of IFN-Y, upon exposure to PD-L205 (PD-L2(16-25)), PD-L2long1 (PD-L2(9-29)), PD-L2long2 (PD-L2(1-25)) and a control HIV peptide (HIV-1 pol476-484).

Finally, to test for spontaneous, PD-L2-specific, CD4+ T-cell responses, we synthesized two longer PD-L2 peptides. One of these, PD-L2long1 (PD-L2(9-29); SLELQLHQIAALFTVTVPKEL, SEQ ID NO: 11), included the PD-L205 (PD-L2(16-25)) epitope; and the other, PD-L2long2 (PD-L2(1-25); MIFLLL-MLSLELQLHQIAALFTVTV, SEQ ID NO: 12), included both the PD-L201 (PD-L2(4-12)) and PD-L205 (PD-L2(16-25)) epitopes. We tested PBMCs from 11 patients with cancer and 11 healthy donors for the presence of CD4+ T cell responses against these long peptides with the IFN-γ ELISPOT assay. We detected frequent but moderate responses (FIG. 3A). Next, we isolated PBMCs from four non-hodgkin lymphoma patients and screened for IFN-γ responses towards PD-L2long2 (PD-L2(1-25)) in an in vitro ELISPOT assay. All four patients showed responses that were statistically significant, according to the DFR rule (FIGS. 3B and 3C). Tumor infiltrating T-lymphocytes from two melanoma patients also elicited IFN-γ CD4+ T-cell responses towards PD-L2long2 (PD-L2(1-25)) measured by using intracellular cytokine staining (FIG. 3D).

PD-L2-Specific T Cells were Effector Cells Releasing Pro-Inflammatory Cytokines

Figure 4:
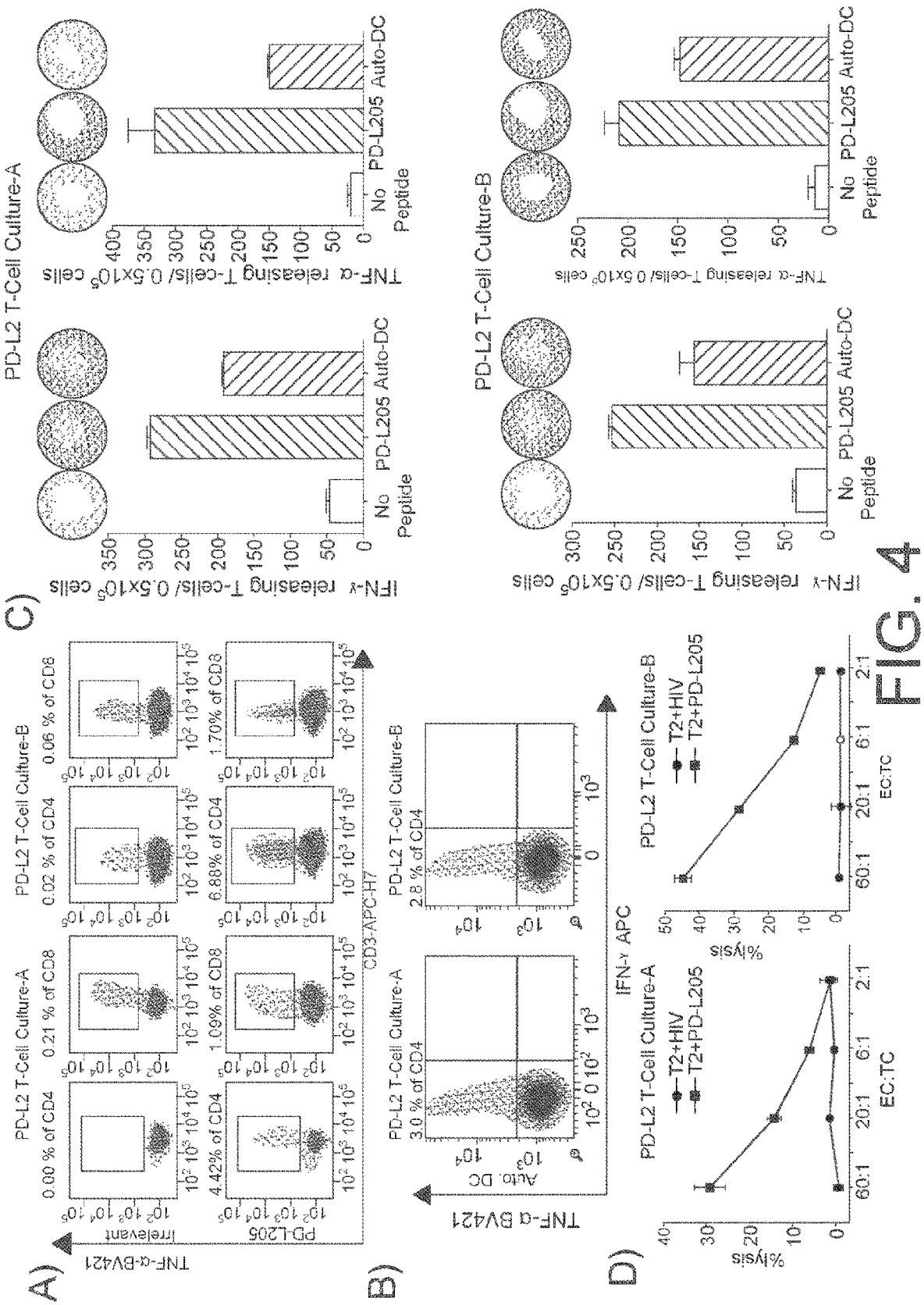
FIG. 4: PD-L2-specific T cells are effector T cells. (A) Intracellular cytokine staining showing CD4+ and CD8+ T cells that release TNF-α in response to either an irrelevant control peptide HIV peptide (HIV-1 pol476-484) or PD-L205 (PD-L2(16-25)) in cultures of PD-L2 T cells-A (left) and PD-L2 T cells-B (right). (B) Intracellular TNF-α and IFN-γ cytokine staining of PD-L2 T-cells culture-A (left) and PD-L2 T-cells culture-B (right) in response to 5 hours stimulation with autologous DCs. (C) IFN-γ and TNF-α secretion by PD-L2 T-cell culture-A (top) and PD-L2 T-cell culture-B (bottom) towards PD-L205 (PD-L2(16-25)) peptide (black bars) and autologous DCs when cultured at ratio 1:5 (grey bars) as measured by ELISPOT assay. (D) T2 cells pulsed either with PD-L205 (PD-L2(16-25)) or a control HIV peptide (HIV-1 pol476-484) as recognized by PD-L2 T-cell culture-A (left) and PD-L2 T-cell culture-B (right) in a standard 51Cr-release assay.

To characterize the immune response elicited by PD-L2, we isolated PD-L205-specific T cells. Briefly, PBMCs isolated from a patient with melanoma (AA26) were expanded in vitro. Then, PBMCs were stimulated with irradiated autologous DCs that had been pulsed with PD-L205. Specific T cells were isolated either by staining with anti-CD137 antibody (PD-L2 T cell culture-A) or with the TNF-α enrichment method (PD-L2 T cell culture-B). These specific T cells were cultured and expanded with high dose IL-2, then analyzed for specificity against PD-L205 (PD-L2(16-25)) with intracellular cytokine staining (FIGS. 4A and 4B), ELISPOT (FIG. 4C) and cytotoxicity assays (FIG. 4D). We detected TNF-α release in response to PD-L205(PD-L2(16-25)) in about 4.5% and 1% of CD4+ and CD8+ T cells, respectively, from PD-L2 T cell culture-A; and about 7% and 2% of CD4+ and CD8+ T cells, respectively, from PD-L2 T cell culture-B (FIG. 4A). Additionally, we detected TNF-α release in response to autologous DCs in around 3% and 2.8% of CD4+ T cells from PD-L2 T cell culture-A and -B respectively (FIG. 4B). Furthermore, IFN-Y and TNF-α T cell responses were observed towards PD-L205 (PD-L2 (16-25)) peptide and autologous DCs in both PD-L2 specific cultures (FIG. 4C). Both expanded cultures also recognized and lysed T2 cells that had been pulsed with PDL205 (PD-L2(16-25)) in conventional 51chromium-release assays, but they did not recognize T2 cells pulsed with an irrelevant HIV peptide (HIV-1 pol476-484) (FIG. 4D).

PD-L2 Dependent Reactivity in Response to PD-L2 Expressing DCs

Figure 5:
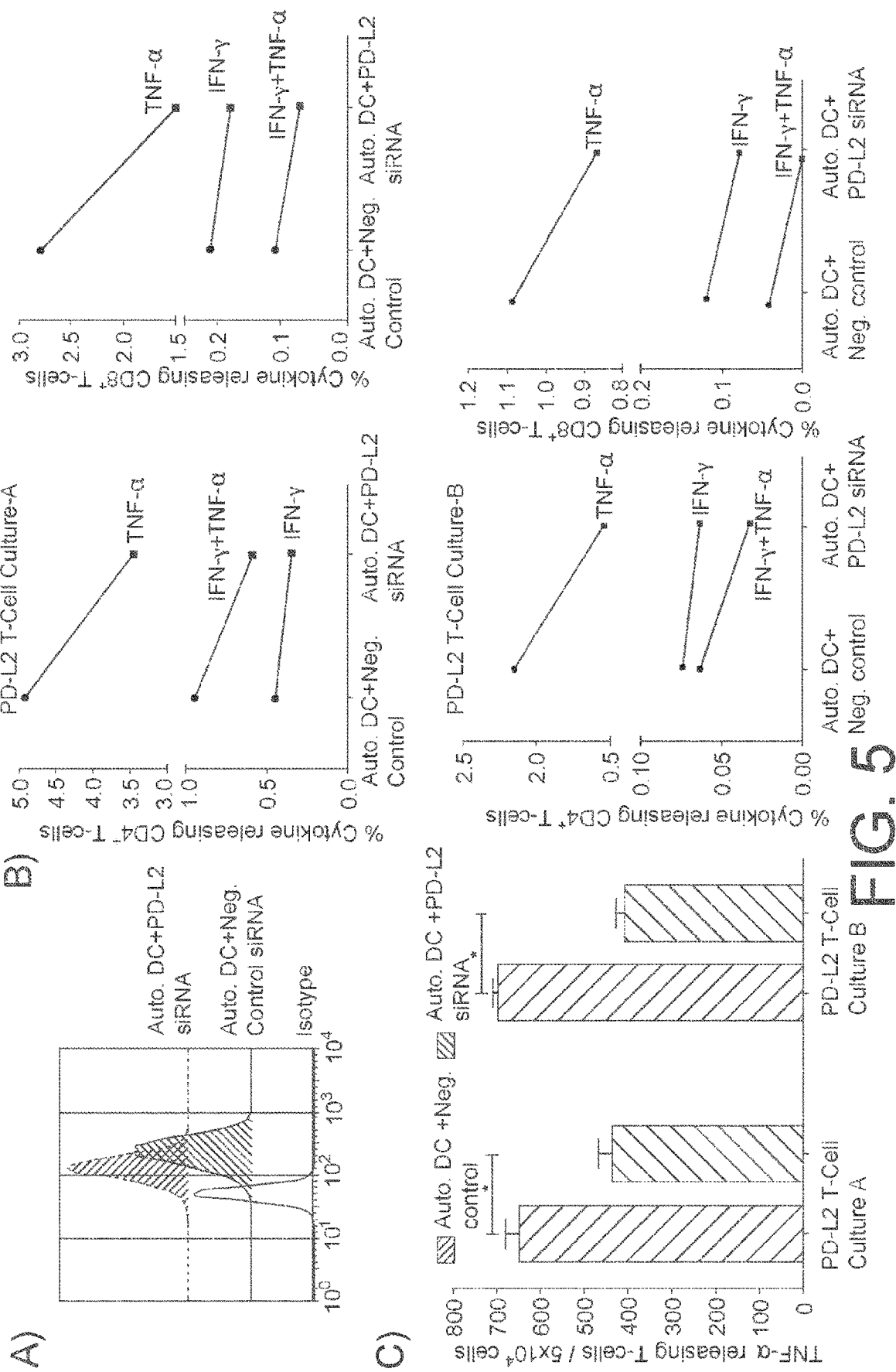
FIG. 5: PD-L2 dependent reactivity towards DCs. (A) Flow cytometric analysis showing profile of PD-L2 surface expression on autologous DCs transfected with either PD-L2 siRNA or negative control siRNA, 48 hr after electroporation. (B) PD-L2 T-cells culture-A (top) and PD-L2 T-cells culture-B (bottom) were stimulated with autologous DCs transfected PD-L2 siRNA or negative control siRNA for 5 hours at a ratio of 1:5 (DC:T-cell). Percentage of cytokine releasing CD4+ T cells (left) and CD8+ T cells (right) was measured using intracellular cytokine staining. (C) Number of TNF-α releasing T cells in PD-L2 cultures in response to autologous DCs transfected with either a negative control siRNA (black bars) or PD-L2 siRNA (grey bars) measured at 48 hours after electroporation using ELISPOT assay. The assay was performed in triplicate and * denotes significant according to the DFR.

PD-L2 can be induced in immune cells. Thus, as the next and very more important step, we addressed the question whether PD-L2-expressing DCs would also be recognized by PD-L2-reactive T cells. To test this notion, we generated autologous DCs; and transfected these with PD-L2 siRNA. We first examined PD-L2 protein expression on the matured siRNA transfected DCs (FIG. 5A). PD-L2 expression was down regulated on DCs transfected with PD-L2 siRNA compared to a negative control siRNA, 48 hours after electroporation (FIG. 5A). Next, we examined reactivity of PD-L2 T-cell cultures in response to the transfected DCs using intracellular cytokine staining (FIG. 5B) and ELISPOT assay (FIG. 5C). Both PD-L2 T cell cultures show reduced CD4+ and CD8+ T-cell cytokine response towards DCs transfected with PD-L2 siRNA compared to a negative control siRNA (FIG. 5B). Similarly in both cultures, the number of TNF-α releasing T cells were significantly reduced in response to DCs transfected with PD-L2 siRNA compared to a negative control siRNA in an TNF-α ELISPOT assay (FIG. 5C). These results confirmed that the reactivity of target cells were dependent on PD-L2 expression.

PD-L1-Specific and PD-L2-Specific T Cells Did not Cross-React

Figure 6:
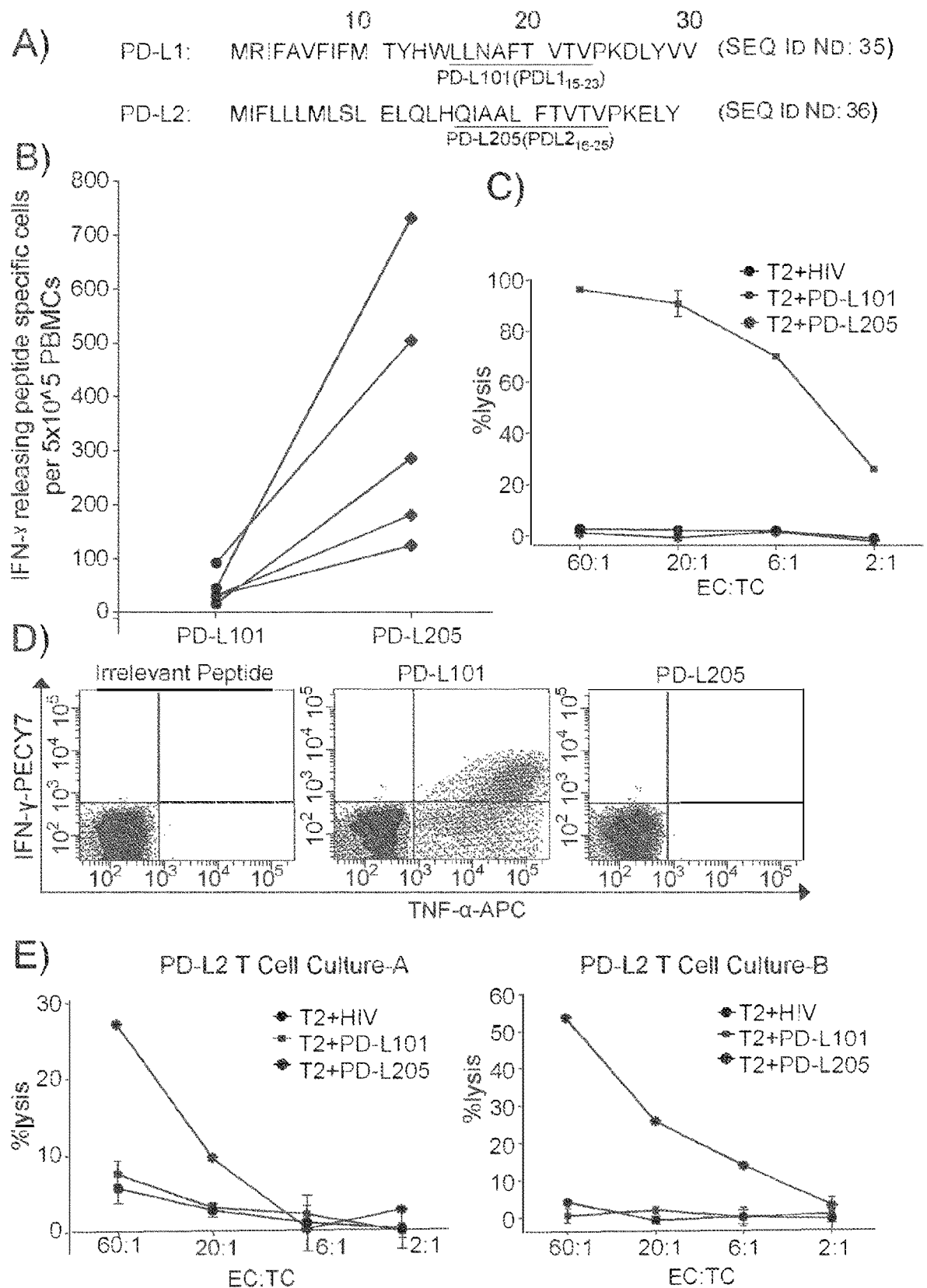
FIG. 6. No cross-reactivity between PD-L1-specific and PD-L2-specific T cells. (A) The first 30 amino acid sequences of PD-L1 and PD-L2 (SEQ ID NO:35 and SEQ ID NO:36) and the location of the peptides PD-L101 (PDL1 (15-23); LLNAFTVTV, SEQ ID NO: 27) and PD-L205 (PD-L2(16-25); QIAALFTVTV, SEQ ID NO: 4) in the signal peptide part of the proteins are marked in bold. (B) In vitro IFN-γ ELISPOT results show responses of T cells from five patients with cancer towards PD-L101 (PDL1(15-23)) and PD-L205 (PD-L2(16-25)) peptides. (C) 51Cr-release assay results show percent lysis of T2 cells pulsed with PD-L101 (PDL1(15-23)), PD-L205 (PD-L2(16-25)), or an irrelevant HIV peptide (HIV-1 pol476-484) when exposed to PD-L101-specific T-cells (CTLs) at different effector-to-target ratios. (D) Intracellular cytokine staining of cultured PD-L101-specific T-cells shows CD8+ T cell release of TNF-α, upon exposure to PD-L101 (PDL1(15-23)), PDL205 (PD-L2(16-25)), or an irrelevant HIV peptide (HIV-1 pol476-484). (E) Percent lysis of T2-cells, pulsed with PDL205 (PD-L2(16-25)), PD-L101 peptide (PDL1(15-23)), or an irrelevant HIV peptide (HIV-1 pol476-484), after exposure to PD-L2 T-cell culture-A (left) or PD-L2 T-cell culture-B (right).

The dominant PD-L2 epitope in eliciting a T cell response was PD-L205 (PD-L2(16-25); QIAALFTVTV, SEQ ID NO: 4). Interestingly, we previously described another HLA-A2 restricted epitope in PD-L1 (termed PD-L101 (PDL1(15-23); LLNAFTVTV, SEQ ID NO: 27) (1), (2), (6), which elicited a strong T cell response. These two dominant T-cell epitopes were located in almost the same position in the PD-L1 and PD-L2 proteins (FIG. 6A). Moreover, these two dominant epitopes shared five amino acids (FTVTV; SEQ ID NO 34), due to sequence similarities between PD-L1 and PD-L2 (FIG. 6A). Thus, we tested for a potential cross reactivity between PD-L205 (PD-L2(16-25))-specific and PD-L101 (PDL1(15-23))-Specific T Cells.

First, we isolated PBMCs from patients with cancer that responded to PD-L205 (PD-L2(16-25)). When we examined whether these PBMCs showed spontaneous T-cell responses against PD-L101 (PDL1(15-23)), we did not detect any immune response with the IFN-γ ELISPOT test (FIG. 6B). Next, we examined the potential cross-reactivity of a PD-L101-specific T-cell culture (1). We used standard 51Cr release assays with TAP-deficient T2 cells as target cells. The target cells were loaded with PD-L101 (PDL1(15-23)), PD-L205 (PD-L2(16-25)), or an irrelevant control peptide from HIV (HIV-1 pol476-484). FIG. 6C illustrates that the PD-L101-specific T cells only lysed T2-cells pulsed with PD-L101 (PDL1(15-23)), and no cytotoxicity was observed against T2-cells pulsed with either PD-L205 (PD-L2(16-25)), or the irrelevant HIV peptide. Next, we performed an intracellular cytokine staining assay to analyze cytokine release (IFN-γ and TNF-α) from PD-L101-specific CD8+ T cells, in response to PDL101 (PDL1(15-23)), PD-L205 (PD-L2(16-25)), or the control HIV peptide (FIG. 5C). Again, we found that PD-L101-specific T cells released cytokines only in response to PD-L101 (PDL1(15-23)) and not in response to PD-L205 (PD-L2(16-25)) or the irrelevant HIV peptide (FIG. 6D).

Finally, we examined whether PD-L205-reactive T cells could specifically recognize PD-L205 (PD-L2(16-25)), but not PD-L101 (PDL1(15-23)). We examined the two established PD-L205-reactive T-cell cultures with the standard 51Cr release assays, with TAP-deficient T2 cells as target cells. The target cells were loaded with PD-L205 (PD-L2 (16-25)), PD-L101 (PDL1(15-23)), or the control HIV peptide (HIV-1 pol476-484). The PD-L205-specific T cells could indeed recognize T2 cells pulsed with PD-L205 (PD-L2(16-25)), but they did not kill T2 cells pulsed with PD-L101 (PDL1(15-23)), or with the control HIV peptide (FIG. 6E).

Discussion

In the present study, PD-L2 was examined as a target for specific T cells, and it was determined that PD-L2-specific T cells are spontaneously present in patients with different cancers including NHL. In general, the strongest responses were elicited by the peptide, PD-L205 (SEQ ID NO 4). Surprisingly, we observed both CD8+ and CD4+ T cells that specifically recognized the minimal epitope in PD-L205 (PD-L2(16-25)), selected for its HLA-A2 peptide binding motif. Interestingly, the PD-L205(PD-L2(16-25)) epitope was similar to the main HLA-A2 restricted epitope that was identified previously in PD-L1. Importantly, PD-L1- and PD-L2-specific T cells did not cross react; therefore, they should be considered different T-cell antigens. The results further showed that PD-L2-specific T cells specifically recognize PD-L2+ target cells. Hence, PD-L2-specific T cells recognize target cells in response to their PD-L2 expression levels. We therefore suggest that inducing/boosting T-cell responses against PD-L2 (e.g., by vaccination) represents an attractive strategy for treating hematologic malignancies, including NHL. These findings justify clinical testing to evaluate the efficacy of a PD-L2-based vaccination. Consequently, applicant is currently initiating the first PD-L2 vaccine study in humans at Herlev Hospital (Denmark). In that study, the long PD-L2 epitope described in this study will be administered to high-risk patients with NHL that are in remission after second-line chemotherapy. This approach represents a major difference from employing monoclonal antibodies to target the PD1/PDL pathway. Indeed, in addition to reducing the direct immunoregulatory effects of PD-L2, these PD-L2-specific T cells might also inhibit other routes of immune suppression that are mediated by PD-L2+ target cells (7).

It was demonstrated that PD-L2-specific T-cells released both IFN-γ and TNF-α. Notably, the investigation found PD-L2 specific T-cell responses directly ex vivo underlining the immunogenicity of this antigen (8). Accordingly, PD-L2-based vaccines should be viewed as complementary, rather than competitive, to other forms of immunotherapy. For example, combining a PD-L2 vaccination with a checkpoint blocker is believed to be an effective therapy. A checkpoint blockade could boost vaccine-activated PD-L2-specific T cells by preventing their inhibition at the tumor site. Likewise, the vaccine-induced upregulation of checkpoint molecules, due to the release of pro-inflammatory cytokines, would also be blocked by the checkpoint inhibitors. Finally, it was found that T cells spontaneously reacted to PD-L2-derived epitopes located in the signal peptide region of PD-L2. Hence, the PD-L2 epitopes recognized by T cells are therefore different than any epitope recognized by anti-PDL2 blocking antibodies. In general, cancer vaccines represent a way to eliminate minimal residual disease without inducing significant toxicity and secondary malignancies. However, to date, they have largely failed to demonstrate a significant improvement in patient outcome (9). This failure probably reflects the ability of malignant cells to suppress the function of the induced immune cells. The addition of PD-L2 epitopes to current cancer vaccine strategies is likely to be highly beneficial, and it would be easy to implement. Furthermore, unlike tumor cells, stromal cell types in the tumor microenvironment are genetically stable, and thus, they represent attractive therapeutic targets with reduced risk of resistance and tumor recurrence.

In conclusion, this present study described naturally-occurring, PD-L2-specific T cells in patients with cancer. PD-L2 may thus serve as a highly accessible target for immunotherapeutic strategies.

Sequences Used in the Specification:

```
Extended PDL2(1-273):
                                                (SEQ ID NO. 1)
MIFLLLMLSLELQLHQIAALFTVTVPKELYIIEHGSNVTLECNFDTGSHV

NLGAITASLQKVENDTSPHRERATLLEEQLPLGKASFHIPQVQVRDEGQY

QCIIIYGVAWDYKYLTLKVKASYRKINTHILKVPETDEVELTCQATGYPL

AEVSWPNVSVPANTSHSRTPEGLYQVTSVLRLKPPPGRNFSCVFWNTHVR

ELTLASIDLQSQMEPRTHPTWLLHIFIPFCIIAFIFIATVIALRKQLCQK

LYSSKDTTKRPVTTTKREVNSAI

PDL2(4-12):
                                                (SEQ ID NO. 2)
LLLMLSLEL

PDL2(231-240):
                                                (SEQ ID NO. 3)
IIAFIFIATV

PDL2(16-25):
                                                (SEQ ID NO. 4)
QIAALFTVTV

PDL2(6-14):
                                                (SEQ ID NO. 5)
LMLSLELQL

PDL2(9-17):
                                                (SEQ ID NO. 6)
SLELQLHQI

PDL2(234-243):
                                                (SEQ ID NO. 7)
FIFIATVIAL

PDL2(11-20):
                                                (SEQ ID NO. 8)
ELQLHQIAAL

PDL2(1-10):
                                                (SEQ ID NO. 9)
MIFLLLMLSL

PDL2(226-235):
                                                (SEQ ID NO. 10)
FIPFCIIAFI

PDL2(9-29):
                                                (SEQ ID NO. 11)
SLELQLHQIAALFTVTVPKEL

PDL2(1-25):
                                                (SEQ ID NO. 12)
MIFLLLMLSLELQLHQIAALFTVTV

PDL2(125-143):
                                                (SEQ ID NO. 13)
KINTHILKV

PDL2(51-59):
                                                (SEQ ID NO. 14)
NLGAITASL

PDL2(54-62):
                                                (SEQ ID NO. 15)
AITASLQKV

PDL2(74-82):
                                                (SEQ ID NO. 16)
TLLEEQLPL

PDL2(30-38):
                                                (SEQ ID NO. 17)
YIIEHGSNV

PDL2(145-153):
                                                (SEQ ID NO. 18)
ATGYPLAEV

PDL2(172-180):
                                                (SEQ ID NO. 19)
GLYQVTSVL

PDL2(168-176):
                                                (SEQ ID NO. 20)
RTPEGLYQV

PDL2(242-251):
                                                (SEQ ID NO. 21)
ALRKQLCQKL

PDL2(31-40):
                                                (SEQ ID NO. 22)
IIEHGSNVTL

PDL2(130-139):
                                                (SEQ ID NO. 23)
ILKVPETDEV

PDL2(149-158):
                                                (SEQ ID NO. 24)
PLAEVSWPNV

PDL2(4-25):
                                                (SEQ ID NO: 25)
LLLMLSLELQLHQIAALFTVTV

HIV-1 pol476-484
                                                (SEQ ID NO: 26)
ILKEPVHGV PDL1(15-23)
                                                (SEQ ID NO: 27)
LLNAFTVTV
```

```
PD-L2 siRNA duplexes
                                        (SEQ ID NO 28)
5'-CAUCCUAAAGGUUCCAGAAtt-3'

(SEQ ID NO 29)
5'-UUCUGGAACCUUUAGGAUGtg3'

(SEQ ID NO 30)
5'-CCUAAGGAACUGUACAUAAtt-3'

(SEQ ID NO 31)
5'-UUAUGUACAGUUCCUUAGGga 3'

(SEQ ID NO 32)
5'-GAAAACAACUCUGUCAAAAtt-3'

(SEQ ID NO 33)
5'-UUUUGACAGAGUUGUUUUCtt 3'

PDL1 and PDL2 epitopes shared five amino acids
                                        (SEQ ID NO 34)
FTVTV
```

REFERENCES

1. Munir S, Andersen G H, Met O, Donia M, Frosig T M, Larsen S K et al. HLA-restricted cytotoxic T cells that are specific for the immune checkpoint ligand PD-L1 occur with high frequency in cancer patients. Cancer Research 2013; 73: 1674-1776.
2. Munir S, Andersen G H, Woetmann A, Odum N, Becker J C, Andersen M H. Cutaneous T cell lymphoma cells are targets for immune checkpoint ligand PD-L1-specific, cytotoxic T cells. Leukemia 2013; 27: 2251-2253.
3. Larsen S K, Munir S, Woetmann A, Froesig T M, Odum N, Svane I M et al. Functional characterization of Foxp3-specific spontaneous immune responses. Leukemia 2013; 27: 2332-2340.
4. Martinenaite E, Ahmad S M, Hansen M, Met O, Westergaard M W, Larsen S K et al. CCL22-specific T cells: Modulating the Immunosuppressive Tumor Microenvironment. Oncoimmunology 2016; 5: e1238541
5. Moodie Z, Price L, Janetzki S, Britten C M. Response determination criteria for ELISPOT: toward a standard that can be applied across laboratories. Methods Mol Biol 2012; 792: 185-196.
6. Ahmad S M, Larsen S K, Svane I M, Andersen M H. Harnessing PD-L1-specific cytotoxic T cells for anti-leukemia immunotherapy to defeat mechanisms of immune escape mediated by the PD-1 pathway. Leukemia 2014; 28: 236-238.
7. Andersen M H. Immune Regulation by Self-Recognition: Novel Possibilities for Anti-cancer Immunotherapy. J Natl Cancer Inst 2015; 107: 154
8. Keilholz U, Weber J, Finke J H, Gabrilovich D I, Kast W M, Disis M L et al. Immuno-logic monitoring of cancer vaccine therapy: results of a workshop sponsored by the Society for Biological Therapy. J Immunother 2002; 25: 97-138.
9. Rhee F. Idiotype vaccination strategies in myeloma: how to overcome a dysfunctional immune system. Clin Cancer Res 2007; 13: 1353-1355.

I claim:

1. A vaccine composition comprising
a peptide, or a pharmaceutically acceptable salt thereof, wherein the peptide is an immunogenic peptide fragment of a human programmed death ligand 2 (PDL2) protein of SEQ ID NO: 1, and consists of a consecutive sequence of up to 60 amino acids of SEQ ID NO: 1, comprises an amino acid sequence selected from SEQ ID NOs: 2, 4, and 11, and does not comprise amino acids 1-3 of SEQ ID NO: 1; and
an adjuvant.

2. The vaccine composition of claim 1, further comprising a pharmaceutically acceptable excipient.

3. The vaccine composition of claim 2, wherein the pharmaceutically acceptable excipient is a preservative.

4. The vaccine composition of claim 1, wherein the adjuvant is selected from the group consisting of a bacterial DNA based adjuvant, an oil/surfactant based adjuvant, a viral dsRNA based adjuvant, and an imidazoquinoline.

5. The vaccine composition of claim 4, wherein the oil/surfactant based adjuvant is a water-in-oil (W/O) emulsion composed of a mineral oil and a surfactant from the mannide monooleate family.

6. The vaccine composition of claim 1, wherein the immunogenic peptide fragment consists of a consecutive sequence from 10 to 17 amino acids, 20 to 30 amino acids, 30 to 40 amino acids, or 40 to 50 amino acids of SEQ ID NO: 1.

7. The vaccine composition of claim 1, wherein the consecutive sequence comprises SEQ ID NO: 11.

8. The vaccine composition of claim 1, wherein the consecutive sequence of SEQ ID NO: 1 comprises SEQ ID NO: 4.

9. The vaccine composition of claim 1, wherein the immunogenic peptide fragment is 9, 10, 11, 12, 13, 14, 15, 16, 17, 18, 19, 20, 21, 22, 23, 24, 25, 26, 27, 28, 29, or 30 amino acids in length.

10. The vaccine composition of claim 1, wherein the immunogenic peptide fragment is an isolated peptide fragment.

11. A vaccine composition comprising a nucleic acid encoding an immunogenic peptide fragment of a human programmed death ligand 2 (PDL2) protein of SEQ ID NO: 1; and a pharmaceutically acceptable additive, wherein the immunogenic peptide fragment consists of a consecutive sequence of up to 60 amino acids of SEQ ID NO: 1, comprises an amino acid sequence selected from SEQ ID NOs: 2, 4, and 11, and does not comprise amino acids 1-3 of SEQ ID NO: 1.

12. The vaccine composition of claim 11, wherein the nucleic acid is comprised within a vector.

13. The vaccine composition of claim 11, wherein the nucleic acid is DNA.

14. The vaccine composition of claim 11, wherein the nucleic acid is RNA.

15. A nucleic acid encoding an immunogenic peptide fragment of a human programmed death ligand 2 (PDL2) protein of SEQ ID NO: 1, wherein the immunogenic peptide fragment consists of a consecutive sequence of up to 60 amino acids of SEQ ID NO: 1, comprises an amino acid sequence selected from SEQ ID NOs: 2, 4, and 11, and does not comprise amino acids 1-3 of SEQ ID NO: 1.

16. The nucleic acid of claim 15, wherein the nucleic acid is DNA.

17. The nucleic acid of claim 15, wherein the nucleic acid is RNA.

18. A vector comprising the nucleic acid of claim 15.

* * * * *

SEQUENCE LISTING

```
Sequence total quantity: 36
SEQ ID NO: 1           moltype = AA  length = 273
FEATURE                Location/Qualifiers
source                 1..273
                       mol_type = protein
                       organism = Homo sapiens
SEQUENCE: 1
MIFLLLMLSL ELQLHQIAAL FTVTVPKELY IIEHGSNVTL ECNFDTGSHV NLGAITASLQ  60
KVENDTSPHR ERATLLEEQL PLGKASFHIP QVQVRDEGQY QCIIIYGVAW DYKYLTLKVK  120
ASYRKINTHI LKVPETDEVE LTCQATGYPL AEVSWPNVSV PANTSHSRTP EGLYQVTSVL  180
RLKPPPGRNF SCVFWNTHVR ELTLASIDLQ SQMEPRTHPT WLLHIFIPFC IIAFIFIATV  240
IALRKQLCQK LYSSKDTTKR PVTTTKREVN SAI                              273

SEQ ID NO: 2           moltype = AA  length = 9
FEATURE                Location/Qualifiers
source                 1..9
                       mol_type = protein
                       note = Peptide fragment of human PDL2
                       organism = synthetic construct
SEQUENCE: 2
LLLMLSLEL                                                         9

SEQ ID NO: 3           moltype = AA  length = 10
FEATURE                Location/Qualifiers
source                 1..10
                       mol_type = protein
                       note = Peptide fragment of human PDL2
                       organism = synthetic construct
SEQUENCE: 3
IIAFIFIATV                                                        10

SEQ ID NO: 4           moltype = AA  length = 10
FEATURE                Location/Qualifiers
source                 1..10
                       mol_type = protein
                       note = Peptide fragment of human PDL2
                       organism = synthetic construct
SEQUENCE: 4
QIAALFTVTV                                                        10
```

```
SEQ ID NO: 5           moltype = AA  length = 9
FEATURE                Location/Qualifiers
source                 1..9
                       mol_type = protein
                       note = Peptide fragment of human PDL2
                       organism = synthetic construct
SEQUENCE: 5
LMLSLELQL                                                                 9

SEQ ID NO: 6           moltype = AA  length = 9
FEATURE                Location/Qualifiers
source                 1..9
                       mol_type = protein
                       note = Peptide fragment of human PDL2
                       organism = synthetic construct
SEQUENCE: 6
SLELQLHQI                                                                 9

SEQ ID NO: 7           moltype = AA  length = 10
FEATURE                Location/Qualifiers
source                 1..10
                       mol_type = protein
                       note = Peptide fragment of human PDL2
                       organism = synthetic construct
SEQUENCE: 7
FIFIATVIAL                                                               10

SEQ ID NO: 8           moltype = AA  length = 10
FEATURE                Location/Qualifiers
source                 1..10
                       mol_type = protein
                       note = Peptide fragment of human PDL2
                       organism = synthetic construct
SEQUENCE: 8
ELQLHQIAAL                                                               10

SEQ ID NO: 9           moltype = AA  length = 10
FEATURE                Location/Qualifiers
source                 1..10
                       mol_type = protein
                       note = Peptide fragment of human PDL2
                       organism = synthetic construct
SEQUENCE: 9
MIFLLLMLSL                                                               10

SEQ ID NO: 10          moltype = AA  length = 10
FEATURE                Location/Qualifiers
source                 1..10
                       mol_type = protein
                       note = Peptide fragment of human PDL2
                       organism = synthetic construct
SEQUENCE: 10
FIPFCIIAFI                                                               10

SEQ ID NO: 11          moltype = AA  length = 21
FEATURE                Location/Qualifiers
source                 1..21
                       mol_type = protein
                       note = Peptide fragment of human PDL2
                       organism = synthetic construct
SEQUENCE: 11
SLELQLHQIA ALFTVTVPKE L                                                  21

SEQ ID NO: 12          moltype = AA  length = 25
FEATURE                Location/Qualifiers
source                 1..25
                       mol_type = protein
                       note = Peptide fragment of human PDL2
                       organism = synthetic construct
SEQUENCE: 12
MIFLLLMLSL ELQLHQIAAL FTVTV                                              25

SEQ ID NO: 13          moltype = AA  length = 9
FEATURE                Location/Qualifiers
source                 1..9
                       mol_type = protein
                       note = Peptide fragment of human PDL2
                       organism = synthetic construct
```

```
SEQUENCE: 13
KINTHILKV                                                                              9

SEQ ID NO: 14              moltype = AA   length = 9
FEATURE                    Location/Qualifiers
source                     1..9
                           mol_type = protein
                           note = Peptide fragment of human PDL2
                           organism = synthetic construct SEQUENCE: 14
NLGAITASL                                                                              9

SEQ ID NO: 15              moltype = AA   length = 9
FEATURE                    Location/Qualifiers
source                     1..9
                           mol_type = protein
                           note = Peptide fragment of human PDL2
                           organism = synthetic construct SEQUENCE: 15
AITASLQKV                                                                              9

SEQ ID NO: 16              moltype = AA   length = 9
FEATURE                    Location/Qualifiers
source                     1..9
                           mol_type = protein
                           note = Peptide fragment of human PDL2
                           organism = synthetic construct SEQUENCE: 16
TLLEEQLPL                                                                              9

SEQ ID NO: 17              moltype = AA   length = 9
FEATURE                    Location/Qualifiers
source                     1..9
                           mol_type = protein
                           note = Peptide fragment of human PDL2
                           organism = synthetic construct SEQUENCE: 17
YIIEHGSNV                                                                              9

SEQ ID NO: 18              moltype = AA   length = 9
FEATURE                    Location/Qualifiers
source                     1..9
                           mol_type = protein
                           note = Peptide fragment of human PDL2
                           organism = synthetic construct SEQUENCE: 18
ATGYPLAEV                                                                              9

SEQ ID NO: 19              moltype = AA   length = 9
FEATURE                    Location/Qualifiers
source                     1..9
                           mol_type = protein
                           note = Peptide fragment of human PDL2
                           organism = synthetic construct SEQUENCE: 19
GLYQVTSVL                                                                              9

SEQ ID NO: 20              moltype = AA   length = 9
FEATURE                    Location/Qualifiers
source                     1..9
                           mol_type = protein
                           note = Peptide fragment of human PDL2
                           organism = synthetic construct SEQUENCE: 20
RTPEGLYQV                                                                              9

SEQ ID NO: 21              moltype = AA   length = 10
FEATURE                    Location/Qualifiers
source                     1..10
                           mol_type = protein
                           organism = synthetic construct SEQUENCE: 21
ALRKQLCQKL                                                                            10

SEQ ID NO: 22              moltype = AA   length = 10
FEATURE                    Location/Qualifiers
source                     1..10
                           mol_type = protein
                           note = Peptide fragment of human PDL2
```

```
                            organism = synthetic construct
SEQUENCE: 22
IIEHGSNVTL                                                                10

SEQ ID NO: 23               moltype = AA  length = 10
FEATURE                     Location/Qualifiers
source                      1..10
                            mol_type = protein
                            note = Peptide fragment of human PDL2
                            organism = synthetic construct
SEQUENCE: 23
ILKVPETDEV                                                                10

SEQ ID NO: 24               moltype = AA  length = 10
FEATURE                     Location/Qualifiers
source                      1..10
                            mol_type = protein
                            note = Peptide fragment of human PDL2
                            organism = synthetic construct
SEQUENCE: 24
PLAEVSWPNV                                                                10

SEQ ID NO: 25               moltype = AA  length = 22
FEATURE                     Location/Qualifiers
source                      1..22
                            mol_type = protein
                            note = Peptide fragment of human PDL2
                            organism = synthetic construct
SEQUENCE: 25
LLLMLSLELQ LHQIAALFTV TV                                                  22

SEQ ID NO: 26               moltype = AA  length = 9
FEATURE                     Location/Qualifiers
source                      1..9
                            mol_type = protein
                            note = HIV-1 (HLA-A2 high affinity binding epitope)
                            organism = synthetic construct
SEQUENCE: 26
ILKEPVHGV                                                                 9

SEQ ID NO: 27               moltype = AA  length = 9
FEATURE                     Location/Qualifiers
source                      1..9
                            mol_type = protein
                            note = PD-L101 (PDL1 peptide)
                            organism = synthetic construct
SEQUENCE: 27
LLNAFTVTV                                                                 9

SEQ ID NO: 28               moltype = DNA  length = 21
FEATURE                     Location/Qualifiers
source                      1..21
                            mol_type = other DNA
                            note = PDL2 siRNA transcript 1 (sense)
                            organism = synthetic construct
misc_feature                1..19
                            note = RNA
misc_feature                20..21
                            note = DNA
SEQUENCE: 28
catcctaaag gttccagaat t                                                   21

SEQ ID NO: 29               moltype = DNA  length = 21
FEATURE                     Location/Qualifiers
source                      1..21
                            mol_type = other DNA
                            note = PDL2 siRNA transcript 1 (antisense)
                            organism = synthetic construct
misc_feature                1..19
                            note = RNA
misc_feature                20..21
                            note = DNA
SEQUENCE: 29
ttctggaacc tttaggatgt g                                                   21

SEQ ID NO: 30               moltype = DNA  length = 21
FEATURE                     Location/Qualifiers
source                      1..21
                            mol_type = other DNA
```

```
                                note = PDL2 siRNA transcript 2 (sense)
                                organism = synthetic construct
misc_feature                    1..19
                                note = RNA
misc_feature                    20..21
                                note = DNA
SEQUENCE: 30
cctaaggaac tgtacataat t                                                   21

SEQ ID NO: 31           moltype = DNA  length = 21
FEATURE                 Location/Qualifiers
source                  1..21
                        mol_type = other DNA
                        note = PDL2 siRNA transcript 2 (antisense)
                        organism = synthetic construct
misc_feature            1..19
                        note = RNA
misc_feature            20..21
                        note = DNA
SEQUENCE: 31
ttatgtacag ttccttaggg a                                                   21

SEQ ID NO: 32           moltype = DNA  length = 21
FEATURE                 Location/Qualifiers
source                  1..21
                        mol_type = other DNA
                        note = PDL2 siRNA transcript 3 (sense)
                        organism = synthetic construct
misc_feature            1..19
                        note = RNA
misc_feature            20..21
                        note = DNA
SEQUENCE: 32
gaaaacaact ctgtcaaaat t                                                   21

SEQ ID NO: 33           moltype = DNA  length = 21
FEATURE                 Location/Qualifiers
source                  1..21
                        mol_type = other DNA
                        note = PDL2 siRNA transcript 3 (antisense)
                        organism = synthetic construct
misc_feature            1..19
                        note = RNA
misc_feature            20..21
                        note = DNA
SEQUENCE: 33
ttttgacaga gttgttttct t                                                   21

SEQ ID NO: 34           moltype = AA   length = 5
FEATURE                 Location/Qualifiers
source                  1..5
                        mol_type = protein
                        note = Amino acids shared between PDL1 and PDL2
                        organism = synthetic construct
SEQUENCE: 34
FTVTV                                                                      5

SEQ ID NO: 35           moltype = AA   length = 30
FEATURE                 Location/Qualifiers
source                  1..30
                        mol_type = protein
                        note = Peptide fragment of PD-L1
                        organism = synthetic construct
SEQUENCE: 35
MRIFAVFIFM TYHWLLNAFT VTVPKDLYVV                                           30

SEQ ID NO: 36           moltype = AA   length = 30
FEATURE                 Location/Qualifiers
source                  1..30
                        mol_type = protein
                        note = Peptide fragment of PD-L2
                        organism = synthetic construct
SEQUENCE: 36
MIFLLLMLSL ELQLHQIAAL FTVTVPKELY                                           30
```